(12) United States Patent
Muller et al.

(10) Patent No.: US 8,981,053 B2
(45) Date of Patent: Mar. 17, 2015

(54) MOLECULES SPECIFICALLY BINDING PANCREATIC BETA CELLS BIOMARKERS

(75) Inventors: Robert Muller, Mons (BE); Decio L. Eizirik, Dilbeek (BE); Corine Sermeus, Silly (BE); Sophie Laurent, Boussu (BE); Carmen Burtea, Mons (BE); Marie-Claire Beckers, Angleur (BE); Daisy Flamez, Sint-Kwintens-Lennik (BE)

(73) Assignees: Universite de Mons, Mons (BE); Université Libre de Bruxelles, Bruxelles (BE); Eurogentec SA, Seraing (BE)

( * ) Notice: Subject to any disclaimer, the term of this patent is extended or adjusted under 35 U.S.C. 154(b) by 0 days.

(21) Appl. No.: 14/125,689

(22) PCT Filed: Jun. 22, 2012

(86) PCT No.: PCT/EP2012/062093
§ 371 (c)(1),
(2), (4) Date: Dec. 12, 2013

(87) PCT Pub. No.: WO2012/175676
PCT Pub. Date: Dec. 27, 2012

(65) Prior Publication Data
US 2014/0105823 A1    Apr. 17, 2014

(30) Foreign Application Priority Data
Jun. 23, 2011  (EP) .................................. 11171180

(51) Int. Cl.
*C07K 7/00*      (2006.01)
*A61K 38/00*     (2006.01)
*C07K 14/00*     (2006.01)
*C07K 14/47*     (2006.01)
*G01N 33/569*    (2006.01)
*A61K 49/00*     (2006.01)

(52) U.S. Cl.
CPC ........... *C07K 14/001* (2013.01); *C07K 14/4713* (2013.01); *G01N 33/56966* (2013.01); *A61K 49/0004* (2013.01)
USPC ......................................... 530/324; 514/21.3

(58) Field of Classification Search
None
See application file for complete search history.

(56) References Cited

U.S. PATENT DOCUMENTS

2005/0050656 A1 *  3/2005  Huang et al. ..................... 8/406

FOREIGN PATENT DOCUMENTS

| WO | WO2008004104 A1 * | 4/2008 |
| WO | WO 2009/101181 A2 | 8/2009 |
| WO | WO 2009101181 A2 * | 8/2009 |
| WO | WO 2010/096930 A1 | 9/2010 |

OTHER PUBLICATIONS

International Search Report and Written Opinion of the International Searching Authority for International Application No. PCT/EP2012/062093, mailed on Jan. 30, 2013.

* cited by examiner

*Primary Examiner* — James H Alstrum Acevedo
*Assistant Examiner* — Jeanette Lieb
(74) *Attorney, Agent, or Firm* — Knobbe, Martens, Olson & Bear LLP

(57) ABSTRACT

The present invention provides a synthetic peptide molecule that specifically binds an FXYD2-gamma isoform of pancreatic beta cells, said synthetic peptide molecule has 25 amino acids.

13 Claims, 12 Drawing Sheets

MOLECULES SPECIFICALLY BINDING PANCREATIC BETA CELLS BIOMARKERS

CROSS-REFERENCE TO RELATED APPLICATIONS

This application is the U.S. National Phase under 35 U.S.C. §371 of International Application PCT/EP2012/062093, filed Jun. 22, 2012, which claims priority to EP 11171180.0, filed Jun. 23, 2011.

REFERENCE TO SEQUENCE LISTING

The present application is filed along with a Sequence Listing in electronic format. The Sequence Listing is provided as a file entitled 18783320_1, created Sep. 2, 2014, which is approximately 5.03 KB in size. The information in the electronic format of the Sequence Listing is incorporated herein by reference in its entirety.

FIELD OF THE INVENTION

The present invention is directed to the medical field, in particular to the imaging and quantification of pancreatic beta cell mass, targeting or visualization of pancreatic beta cells for pathology and/or diagnosis of diabetic disorders and to follow up of pancreatic islet transplantation.

BACKGROUND

An estimated 285 million people, corresponding to 6.4% of the world's adult population is affected by diabetes mellitus. The number is expected to increase to 438 million worldwide by 2030, corresponding to 7.8% of the adult population. More than 50 million individuals are affected in Europe. The majority (around 85%) of patients have type 2 diabetes mellitus (T2D), while some 10-15% of the patients suffer from type 1 diabetes mellitus (T1D). It is one of the major causes of premature illness and death worldwide. Diabetes causes severe long-term complications and psychosocial problems, imposing a heavy burden of morbidity and premature mortality. Diabetes is the leading cause of blindness and visual disability, limb amputation, end-stage renal failure and neuropathy. It is associated with a greatly increased incidence of cardiovascular disease, including stroke, myocardial infarction and heart failure. Cardiovascular disease accounts for more than 50% of all deaths among diabetic patients in Europe. Because T2D is increasingly prevalent and developing earlier in life, increasing the duration of the disease by decades, many more people are developing severe diabetic complications, and suffering decreases their life quality and expectancy.

Diabetes incurs many costs, and is particularly expensive because it is life-long and causes major medical problems. These costs include direct costs from physician and nursing services, hospital services, laboratory services, drugs, education and training of the patients and indirect costs from time lost from work, chronic nursing and general socio-economic support, early retirement, protracted morbidity and premature mortality.

Overall costs of diabetes mellitus, comprising both direct and indirect costs, have been calculated in various countries and are enormous. For instance, the cost of treating one patient over a 25-year period is in the range of 100,000-200,000 EURO.

The pancreas, an organ about the size of a hand, is located behind the lower part of the stomach. It comprises two structures that are both morphologically and physiologically different: the exocrine pancreas, which produces the enzymes involved in digestion (amylase, lipase, etc.) and sodium bicarbonate, and the endocrine pancreas, which produces the hormones involved in the control of blood glucose (insulin, glucagon, somatostatin and pancreatic polypeptide). The cells of the endocrine pancreas are organized as micro-organs dispersed in the pancreas in the form of islets (islets of Langerhans or pancreatic islets). Each pancreatic islet is made up of 4 cell types: alpha cells, beta cells, delta cells and PP cells. In rats, the alpha cells are located at the periphery of the islet and secrete glucagon. The beta cells are found at the center of the islet and are the only cells capable of secreting insulin in response to glucose. The delta cells are at the periphery and secrete somatostatin. In humans, the cells are scattered inside the Langerhans islets. The function of the PP cells is more controversial (synthesis of pancreatic polypeptide).

Insulin is a hormone that helps the body to use glucose for energy. Diabetes develops when the body does not make enough insulin, cannot use insulin properly, or both, causing glucose to build up in the blood. In type 1 diabetes mellitus (T1D)—an autoimmune disease—the beta cells of the pancreas no longer make insulin because the body's immune system has attacked and destroyed them. A person who has T1D must take insulin daily to live. Type 2 diabetes mellitus (T2D) usually begins with a condition called insulin resistance, in which the body has difficulty using insulin effectively. Over time, insulin production declines as well, so many people with T2D eventually need to take insulin. In addition, a condition called hyperinsulinemia occurs in patients with increased beta cell populations when compared to healthy subjects. Patients with hyperinsulinemia are at high risk of developing seizures, mental retardation, and permanent brain damage. Since glucose is the primary substrate used by the CNS, unrecognized or poorly controlled hypoglycemia may lead to persistent severe neurologic damage. Transient hyperinsulinemia is relatively common in neonates. An infant of a diabetic mother, an infant who is small or large for gestational age, or any infant who has experienced severe stress may have high insulin concentrations.

Among the treatments of diabetes, besides the regular administration of insulin, one of the approaches for the physiological control of glycemia and for normalization of glycemia in diabetics is to restore insulin secretion in vivo from cells. Several strategies have been proposed: xenotransplantation of insulin-producing cells from animals, in vitro differentiation of isolated stem cells into insulin-secreting cells and re-implantation thereof in the patient or allotransplantation of isolated pancreatic islets from another subject.

The lack of a cellular model for studying the beta cells, and also the lack of reliable and effective means of cell sorting suitable for this type of cells hinder the study of beta cell functioning and therefore the development of novel methods of treatment of type I and II diabetes.

The current attempts of imaging pancreatic beta cell mass are being done either by using MRI (magnetic resonance imaging) or by using PET (positron emission tomography) and SPECT (single photon emission computed tomography). In vivo imaging of beta cell mass needs a combination of very high sensitivity and high spatial resolution. MRI has the best spatial resolution but its major challenge is the low sensitivity achieved with magnetic probes and the ex-vivo labeling procedure currently used in islet transplantation. MRI has been successfully used by labeling of human islets with SPIO (small particles of iron oxide) ex vivo and subsequent islet transplantation (Evgenov et al 2006). Using this approach, it was possible to follow up the grafted beta cell mass up to 6
} months after transplantation. This technique is, however, only usable for transplantation since it relies on ex vivo uptake of the marker by islet cells and cannot be used for in vivo imaging of beta cells in the pancreas. MRI was also used for tracking recruitment of diabetogenic CD8+ T-cells into the pancreas (Moore A et al, 2004), for detecting apoptosis in T1D progression using a Cy5.5 labeled annexin 5 probe (Medarova Z. et al, 2006) or for detection of micro vascular changes in T1D progression (Medarova Z. et al 2007), but the changes detected are semi-quantitative.

PET and SPECT have very high sensitivity and do not require ex-vivo labeling. On the other hand, these techniques have a lower spatial resolution as compared to MRI. PET or SPECT imaging is achieved using islet-specific receptor binding compounds or using compounds taken up specifically by transporters in the pancreatic islets labeled with radioactive tracers. Almost all current substrates used for beta cell PET/SPECT imaging bind or are taken up by the non-beta cells and, in some cases, even by exocrine cells in the pancreas. This results in the dilution of tracer and high backgrounds, making it currently impossible to quantify the beta cells which are scattered over the pancreas in tiny islets (100-300 [mu]m diameter) constituting only 1-2% of the total pancreas mass.

One of few beta-cell specific membrane proteins identified up to now is the zinc transporter ZnT8 protein encoded by the SLC30A8 gene (Chimienti F et al 2004, Seve et al 2004). ZnT8 co-localizes with insulin in the pancreatic beta cells (Chimienti et al 2006). Avalon (EP1513951 and WO03097802) and CEA (patent US2006246442, EP1563071 and WO2004046355) introduced patents on the fact that this protein was beta cell specific and on the usage of an antibody against ZnT8 for cancer therapy and for use in antibody test. Recently ZnT8 was identified as an autoantigen and the target of autoantibodies in type 1 diabetes (Wenzlau J M et al., 2007) and it is therefore not useful for beta cell detection.

The company Biogen-IDEC identified Kirrel 2 (filtrin or NEPH3), an immunoglobulin superfamily gene which is specifically expressed in the beta cells of pancreatic islet cells (Sun C. et al, 2003) and in kidney (Rinta-Valkama J et al 2007). Due to its very low expression levels this candidate is not useful for beta cell detection. Recently, it was shown that densin and filtrin can act as auto-antigens, and auto-antibodies against them are detected in T1D patients (Rinta-Valkama J et al 2007). However, this candidate was too lowly expressed to be of use in beta cell detection.

Tmem27 or collectrin was identified as a beta cell protein that stimulates beta cell proliferation (Fukui K et al, 2005) and which is cleaved and shed from the plasma membrane. However, collectrin expression is higher in the islet non beta cells than in the beta cells.

The free fatty acid receptor GPR40 (also called FFAR1) is a G-coupled receptor recently identified as islet specific and as a possible target for treatment of T2D (Bartoov-Shifman R et al 2007). This receptor, however, is expressed both in islet beta cells and in alpha cells (Flodgren E et al 2007), hampering its potential as a good beta cell biomarker.

PET imaging teams working on pancreas are also attempting to image beta cells. For this purpose, they are using compounds assumed to selectively bind or being taken up by islet-specific transporters and receptors. Examples of these compounds include glibenclamide, tolbutamide, serotonin, L-DOPA, dopamine, nicotinamide, fluorodeoxyglucose, and fluorodithizone. Glibenclamide and fluorodithizone are not specific enough to attain the robust signal to background ratio needed for quantification of beta cell mass via PET imaging. F-deoxy glucose (FDG) could not be used to successfully quantify beta cell mass (Malaisse W J et al. 2000, Ruf J et al. 2006, Nakajo M. et al., 2007) but could be used to discriminate between focal and diffuse hyperinsulinism (de Lonlay P et al 2005 and 2006, Otonkoski T et al 2006, Kauhanen S et al 2007, Ribeiro M J et al, 2007, Hardy OT., et al 2007).

The most promising compounds used up to now to image pancreatic beta cells are F18-DOPA and Dihydrotetrabenazine (DTBZ), both substrates being taken up by the VMAT2 transporter (Souza F. et al 2006, Simpson N R. et al. 2006), and Glucagon-like peptide 1 (GLP-1) or exendin, both ligands binding to the GLP-1 receptor (Gotthardt M. et al, 2002, Wild M. et al. 2006). Unfortunately, all the compounds mentioned above result in too high background levels and non-specific binding to various other intra-abdominal tissues such as kidney and liver.

As described above, the team of Paul Harris identified vesicular monoamine transporter 2 (VMAT2) and its ligand DTBZ as potential tools for beta cell imaging. DTBZ was labeled with C-11 and F-18 and a high pancreatic uptake was obtained in rodents and primates (Souza et al, 2006). Unfortunately, complete eradication of beta cells reduced the pancreatic uptake of DTBZ by only 30-40% showing that the compound lacks sufficient specificity for the beta cells (Kung et al 2007) to enable its use to assess beta cell mass.

Several auto-antibodies directed against insulin (K14D10), sulfatide (IC2), glutamic acid decarboxylase (GAD) or protein tyrosine phosphatase (IA2) have been identified. The team of Ian Sweet used a beta cell specific antibody (K14D10) and its Fab fragment for imaging/targeting beta cells but the antibody fragment with the best blood clearance failed to preferentially accumulate in the pancreas. The monoclonal antibody IC2 (Brogren C H et al 1986, Buschard K et al 1988), modified with a radioisotope chelator for nuclear imaging, showed highly specific binding and accumulation to beta-cells with virtually no binding to exocrine pancreas or stromal tissues (Moore A et al, 2001). Sulfatide, however, is also expressed in islet cell innervating Schwann cells and other neural tissues, which may hamper its use in beta cell imaging.

WO 2009/101181 discloses biomarkers located in the plasma membrane of pancreatic beta cells. These biomarkers are FXYD2 gamma isoforms a, b and c. FXYD2 is a regulating subunit of the Na, K-ATPase. The biomarkers are characterized by their 1) preferential expression in pancreatic islets as compared to surrounding tissues (total pancreas/ exocrine tissue, liver, intestine, spleen, stomach) 2) higher expression in pancreatic beta cells than in pancreatic alpha cells or than in other islet non-beta cells 3) higher or comparable expression levels to glucokinase which is an enzyme specifically expressed in the pancreatic beta cell 4) location in the membrane and as such targetable with antibodies, peptides or small molecules, which allows imaging, targeting and immunohistochemistry and 5) expression is not induced during the process of inflammation of the beta cell mass and the protein is not enriched in T-cells and dendritic cells or in other cells participating in the inflammation process. WO 2009/ 101181 describes the use of antibodies for the detection of these biomarkers in order to allow the early identification of loss in beta cell mass and the follow up of therapies for diabetes, including islet transplantation, attempts at beta cell regeneration etc. Our experiments showed that the antibody described in WO 2009/101181 is not highly specific to the beta cells FXYD2 biomarker. The use of antibodies has several drawbacks. Indeed, besides their long manufacturing process, their specificity and affinity to the target might be low, especially for polyclonal antibodies. The accessibility of the target to heavy antibodies is reduced. Antibodies synthesized in animals (rabbits, rats) might cause an immune response when tested on humans. Moreover, antibodies are subject to degradation.

The present invention aims at providing a peptide that specifically binds a pancreatic beta cell marker, more precisely the FXYD2-gamma-a subunit, and avoiding all the mentioned disadvantages related to the use of antibodies. The invention provides also the use of the peptide in several applications which will be detailed hereafter.

SUMMARY

The present invention relates to peptide molecules that specifically bind an FXYD2-gamma isoform of pancreatic beta cells. The peptide molecules comprises between 3 and 35 amino acids, preferably between 5 and 30 amino acids, more preferably about 25 amino acids.

The peptide molecules directed against the FXYD2-gamma isoform beta cell biomarker will allow beta cell specific mass quantification, evaluate the progression of diabetes/pancreatic cancer and will lead to earlier prediction of pancreatic disease state, allow earlier intervention and thus higher chance to halt diabetes, and enable the follow up of beta cell mass following islet transplantation.

Imaging/targeting strategies using the peptide molecule of the present invention will allow beta cell specific mass quantification, evaluate the progression of diabetes/pancreatic cancer and will lead to earlier prediction of pancreatic disease state, allow earlier intervention and higher chance to halt diabetes, and enable the follow up of beta cell mass following islet transplantation.

Another application of the peptide molecules of the present invention will be the follow up of beta cell mass in patients with type 1 and type 2 diabetes and following islet transplantation. Beta cell imaging will be also useful as a surrogate marker for clinical trials of new therapies aiming to prevent beta cell mass loss in diabetes or to restore beta cell mass by regeneration.

In a preferred embodiment, the present invention provides peptide molecules that specifically bind the FXYD2-gamma-a isoform of pancreatic beta cells.

In a preferred embodiment of the present invention, the peptide molecules comprise synthetic peptide molecules. This advantageous as the production process of synthetic peptide is easier and cheaper compared to the production of antibodies. Also a synthetic peptide is more stable than an antibody. The accessibility, specificity and affinity of a synthetic peptide to a target are higher and more ensured compared to polyclonal antibodies. Moreover, the risk of inducing an immune response is not present as the peptides are not synthesized in animals as for antibodies.

In a further preferred embodiment of the present invention, the peptide molecules are selected from peptides of the following formula and the functional equivalents thereof 1-X2-X3-X4-X5-X6-X7-X8-X9-X10-X11-X12-X13-X14-X15-X16-X17-X18-X19-X20-X21-X22-X23-X24-X25 (SEQ ID NO: 1), wherein X1 is leucine or isoleucine, X2 is proline, X3 is leucine or isoleucine, X4 is serine or threonine, X5 is arginine, lysine or histidine, X6 is histidine, arginine or lysine, X7 is tyrosine, X8, X9 and X10 are glycine, X11 is serine or threonine, X12 is valine, leucine or isoleucine, X13 is proline, X14 phenylalanine or leucine, X15 is tyrosine, X16 is serine or threonine, X17 is histidine, arginine or lysine, X18 is serine or threonine, X19 is asparagine or glutamine, X20 is threonine or serine, X21 and X22 are histidine, arginine or lysine, X23 is threonine or serine, X24 is serine or threonine, X25 is methionine or cysteine, preferably the peptide formula is LPLSRHYGGGSVPFYSHSNTHHTSM (SEQ ID NO: 2) and the functional equivalents thereof.

In a further preferred embodiment of the present invention, the peptide molecules are selected from the peptides of the following formula X26-X27-X28-X29-X30-X31-X32-G-G-G-S-V-P-F-Y-S-H-S-X33-X34-X35-X36-X37-X38-X39 (SEQ ID NO: 3) and the functional equivalents thereof wherein X26 is histidine, arginine or lysine, X27 is aspartic acid or glutamic acid, X28 is arginine, lysine or histidine, X29 is leucine or isoleucine, X30 is lysine, arginine or histidine, X31 is serine or threonine, X32 is histidine, lysine or arginine, X33 is isoleucine or leucine, X34 is histidine, arginine or lysine, X35 is alanine, X36 is histidine, lysine or arginine, X37 is leucine or isoleucine, X38 is proline, X39 is glutamine or asparagine, preferably the peptide formula is HDRLKSHGGGSVPFYSHSIHAHLPQ (SEQ ID NO: 4) and the functional equivalents thereof.

In another embodiment, the present invention provides for the use of peptide molecules for specifically measuring pancreatic beta cell mass.

In another embodiment, the present invention provides for the use of peptide molecules for pancreatic beta cell labeling, wherein at least one peptide molecule is coupled to an iron oxide contrast agent.

In a further embodiment, the present invention provides for the use of peptide molecules, wherein said iron oxide contrast agent has a coating comprising at least a polysiloxane shell and at least one carboxylic acid group.

In another embodiment, the present invention provides a method for measuring pancreatic beta-cell mass comprising the steps of: a) visualizing the beta cells in a sample using peptide molecules, wherein said peptide molecules are labeled, b) quantifying the amount of labeled beta cells.

In another embodiment, the present invention provides for the use of peptide molecules in the preparation of a diagnostic composition for the in-vivo and in-vitro diagnosis of pancreatic beta-cell related disorders.

In another embodiment, the present invention provides a method of in vivo diagnosing a beta-cell-related disorder comprising the following steps: a) introducing into a subject peptide molecules, wherein said peptide molecules are labeled, b) visualizing the peptide molecules specifically located to the beta cell population in the pancreas using PET, PET-CT or SPECT or MRI in vivo, c) quantifying the beta cells mass in said subject, d) comparing of the beta cell mass data obtained in step c) with the beta cell mass of a healthy subject, or of a previous analysis of the same subject, e) diagnosing the subject as having diabetes or being at risk of having diabetes when the level of beta cell mass obtained in step c) is reduced as compared to that of a healthy subject and diagnosing the subject as having hyperinsulinemia or being at risk of having hyperinsulinemia when the level of beta cell mass obtained in step c) is increased as compared to that of a healthy subject, or of a previous analysis of the same subject.

In another preferred embodiment, the present invention provides for the use or a method wherein the beta-cell-related disorder is type 1 diabetes mellitus, type 2 diabetes mellitus, hyperinsulinemia or pancreatic cancer.

In another embodiment, the present invention provides for the use of peptide molecules in the carrying of other molecules to the pancreas.

In another embodiment, the present invention provides a method for targeting molecules to the pancreas comprising the steps of: binding said molecule to peptide molecules b) introducing said molecules bound to the peptide molecules into a subject.

In another embodiment, the present invention provides a kit for specifically measuring beta cell-mass, and/or for diagnosing a beta-cell-related disorder, and/or for purifying beta cells in a subject comprising at least labeled peptide molecules specifically binding to the biomarker FXYD2-gamma-a.

In another embodiment, the present invention provides a method for following up the success of the transplantation of beta cells in a subject comprising the following steps: a) measuring the pancreatic beta-cell mass in the subject in a certain period of time after transplantation of the subject with beta cells, b) determining the success of the transplantation by comparing the beta cell mass in the course of time.

In another embodiment, the present invention provides a method for purifying or isolating beta cells from other pancreatic non-beta cells comprising the following steps: a) tagging the beta cells with peptide molecules, wherein said peptide molecules are labeled, b) isolating the labeled cells from the non-labeled cells through the tag on the beta cells, thereby obtaining a substantially pure beta cell preparation.

In another embodiment, the present invention provides a method for identification of regeneration of beta cells comprising the steps of: a) tagging the beta cells with peptide molecules, wherein said peptide molecules are labeled, b) isolating the labeled cells from the non-labeled cells through the tag on the beta cells, thereby obtaining a substantially pure regenerated beta cell preparation, c) performing immunohistochemistry to identify the number of newly regenerated beta cells and to define the new beta cell mass, d) follow up of therapeutic strategies and detect beta cell mass recovery.

In another embodiment, the present invention provides a method for identification of stem cell populations in order to derive functional insulin-expressing cells comprising the following steps: a) tagging the beta stem cells with peptide molecules, wherein said peptide molecules are labeled, b) isolating the labeled cells from the non-labeled cells through the tag on the potential beta stem cells, thereby obtaining a substantially pure beta stem cell preparation.

In a preferred embodiment, the present invention provides a method for identification of stem cell populations further comprising the steps of: c) performing immunohistochemistry to identify the number of beta stem cells, and to define the new beta cell mass, d) follow up of therapeutic strategies and detect newly formed beta cell mass.

DETAILED DESCRIPTION OF THE INVENTION

Figure 1:
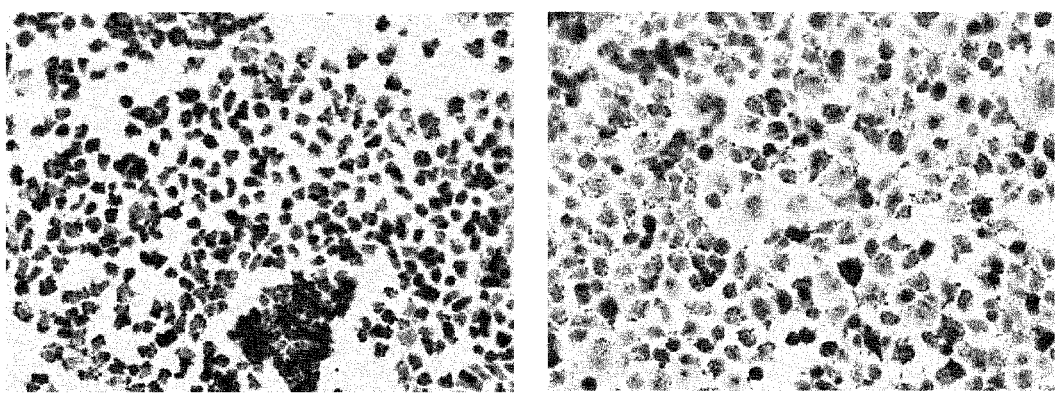
FIG. 1 Immunocytochemistry test performed on CAPAN2 cells (left panel) and PANC1 cells (right panel) using a polyclonal antibody against the N-terminal sequence of FXYD2-gamma-a protein.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

The terms labeling and marking are used herein as synonyms.

The present invention relates to peptide molecules that specifically bind an FXYD2-gamma isoform of pancreatic beta cells comprising between 3 and 35 amino acids, preferably between 5 and 30 amino acids, more preferably about 25 amino acids. In a more preferred embodiment, the peptide molecule specifically binds the FXYD2-gamma-a isoform. In a further preferred embodiment, the peptide molecule specifically binds the FXYD2-gamma-a isoform of human pancreatic beta cells.

Methods of identifying peptide molecules comprise two-hybrid analysis, phage display, immunoprecipitation methods and the like.

The identification of binding peptide molecules of the present invention can be performed using cells or cell-lines that do or do not express the FXYD2-gamma marker. FXYD2-gamma-a positive cells and/or cell-lines might be rodent pancreatic islets, rat INS-1 E, AR42J cells or human CAPAN-2 cells and FXYD2-gamma-a negative cell-line might be human pancreatic alpha cells or human PANC-1 cells. These cells or cell-lines can be used to screen for peptide molecules that specifically bind to FXYD2-gamma-a positive cells, but not to FXYD2-gamma-a negative cells in order to identify new tracer peptide molecules for visualization of beta-cell mass in PET, PET-CT or SPECT analysis.

In one such aspect, the invention provides a method for identifying new peptide molecules that specifically bind FXYD2-gamma-a positive cells comprising the steps of: a) contacting the candidate peptide molecules with the FXYD2-gamma-a positive cell-type or cell-line and measure the interaction between the candidate peptide molecules and the cells; b) contacting the candidate peptide molecules with the FXYD2-gamma-a negative cell-type or cell-line and measure the interaction between the candidate tracer molecule and the cells; c) wherein these candidate peptide molecules that bind the cells of step a) but not the cells of step b) are retained as beta-cell-mass tracer molecules. In a preferred embodiment of said method, the FXYD2-gamma-a positive cell-type or cell-line is selected from the group consisting of: rodent pancreatic islets, rat INS-1 E, AR42J cells and human CAPAN-2 cells; and the FXYD2-gamma negative cell-type or cell-line might be human pancreatic alpha cells or human PANC-1 cells.

In a further preferred embodiment, the peptide molecules of the present invention are selected from a commercially available peptide library using the phage display, a very well-known method in the art. The phage display method is a technology used for studying interactions of proteins. This technology is based on expressing on the surface of a phage the binding protein of interest and selecting said binding protein on its capacity to form a complex with a binding partner. The principle of this method relies on the genetic recombination of the phage genome: a sequence encoding a binding protein of interest is inserted into said phage genome. The sequence insertion is localized next to a gene encoding a protein forming the coat protein complex of the phage. The foreign sequence is generally spliced inside said gene, between the region encoding for the signal peptide and the mature protein. Said coat is composed of different proteins, such as for example pIII and pVIII proteins which are the most commonly used. The insertion of a sequence of interest next to the gene encoding these proteins enables the fusion of the binding protein of interest to the coat protein of the phage. The recombinant phage then infects bacteria, and its genome is replicated. The expression of the recombinant phagic genome leads to the production of phages expressing on their surface the binding protein to be screened. During the steps of screening, different proteins or molecules, referred to as binding partners, are brought into contact with said protein of interest. When a complex is formed between the binding protein or peptide on the surface of the phage and a binding partner, the complex is purified and the nucleotidic sequence encoding the binding protein of interest can then be determined from the recombinant phagic genome.

In a further preferred embodiment of the present invention, the peptide molecules are selected from peptides of the following formula and the functional equivalents thereof1-X2-X3-X4-X5-X6-X7-X8-X9-X10-X11-X12-X13-X14-X15-X16-X17-X18-X19-X20-X21-X22-X23-X24-X25 (SEQ ID NO: 1), wherein X1 is leucine or isoleucine, X2 is proline, X3 is leucine or isoleucine, X4 is serine or threonine, X5 is arginine, lysine or histidine, X6 is histidine, arginine or lysine, X7 is tyrosine, X8, X9 and X10 are glycine, X11 is serine or threonine, X12 is valine, leucine or isoleucine, X13 is proline, X14 phenylalanine or leucine, X15 is tyrosine, X16 is serine or threonine, X17 is histidine, arginine or lysine, X18 is serine or threonine, X19 is asparagine or glutamine, X20 is threonine or serine, X21 and X22 are histidine, arginine or lysine, X23 is threonine or serine, X24 is serine or threonine, X25 is methionine or cysteine, preferably the peptide formula is LPLSRHYGGGSVPFYSHSNTHHTSM (SEQ ID NO: 2) and the functional equivalents thereof.

In a further preferred embodiment of the present invention, the peptide molecules are selected from the peptides of the following formula X26-X27-X28-X29-X30-X31-X32-G-G-G-S-V-P-F-Y-S-H-S-X33-X34-X35-X36-X37-X38-X39 (SEQ ID NO: 3) and the functional equivalents thereof wherein X26 is histidine, arginine or lysine, X27 is aspartic acid or glutamic acid, X28 is arginine, lysine or histidine, X29 is leucine or isoleucine, X30 is lysine, arginine or histidine, X31 is serine or threonine, X32 is histidine, lysine or arginine, X33 is isoleucine or leucine, X34 is histidine, arginine or lysine, X35 is alanine, X36 is histidine, lysine or arginine, X37 is leucine or isoleucine, X38 is proline, X39 is glutamine or asparagine, preferably the peptide formula is HDRLK-SHGGGSVPFYSHSIHAHLPQ (SEQ ID NO: 4) and the functional equivalents thereof.

In another embodiment, the peptide molecules of the present invention are used in the estimation and visualization of the pancreatic beta cell mass in health and diseased state (diabetes or following islet transplantation). The invention will allow the development of tools for prediction and follow up of the diabetic state, for the follow up of islet transplantation, and as surrogate measures for therapeutic assays aiming to prevent diabetes and/or regenerate beta cell mass.

In a further embodiment, the present invention provides a method of in vivo diagnosing a beta-cell-related disorder wherein at least one peptide molecule is bound to a contrast agent, thus forming an imaging probe. The success of various treatment strategies in type 1 (classical treatment with insulin, as well newly developed therapeutic strategies) or type 2 (decrease of insulin resistance, stimulation of insulin production, prevention of carbohydrate digestion, as well newly developed therapeutic strategies) diabetes, as well as in pancreas adenocarcinoma (radiotherapy, chemotherapy, surgery) is monitored. The contrast agent is any particulate or nanoparticle known in the art such as SPIO, USPIO or any other coated nanoparticle or paramagnetic contrast agent for MRI or radioactive probes for PET, PET-CT, SPECT. Preferably, the peptide molecules of the present invention are coupled to nanoparticles developed by the inventors and described hereafter.

The nanoparticles developed by the inventors are based on small iron oxide cores coated with a thin polysiloxane shell presenting carboxylic acid groups and used as MRI $T_2$ contrast agents. The thickness of the coating is comprised between 0.1 nm and 1.2 nm, preferably between 0.2 nm and 1 nm, more preferably between 0.3 nm and 0.8 nm, more preferably about 0.5 nm. An aqueous solution of these electrostatically stabilized nanoparticles can be concentrated up to 70% wt. The produced nanoparticles have a hydrodynamic diameter comprised between 19 nm and 40 nm, preferably between 20 nm and 25 nm, more preferably about 21 nm. These nanoparticles are characterized by a low colloidal stability in cell culture media and a high stability in saline solution and are therefore easily re-dispersed in phosphate buffer saline solution (PBS) to obtain properly labeled cells.

These coated iron oxide nanoparticles are produced via a simple method at the gram scale with a stabilization shell based on carboxy silane. Iron oxide cores are obtained by the polyol method, which consists in the precipitation of metal oxide in high boiling alcohol. Adding solid NaOH to iron chloride salts dissolved in diethyleneglycol (DEG) leads to a black precipitate of agglomerated iron oxide nanoparticles that can be washed and suspended in acidic media. To stabilize the iron oxide nanoparticles, triethoxysilanepropyl succinic acid (TESPSA) is used. Silanol groups react with hydroxyl groups at the iron oxide surface to form a Si—O—Fe link. Iron oxide nanoparticles are thus transferred into dimethylformamide (DMF) by simple elimination of water under low pressure and heating. This step allows controlling the hydrolysis of silane's alkoxy groups by addition of known amounts of water in the reaction media.

In another preferred embodiment, the peptide molecules of the present invention are used for specifically measuring pancreatic beta cell mass.

In another preferred embodiment, the present invention provides a method for measuring pancreatic beta-cell mass comprising the steps of: a) visualizing the beta cells in a sample using the peptide molecules, wherein said peptide molecules are labeled, b) quantifying the amount of labeled beta cells. Imaging probes are conceived for multimodal (MRI/fluorescent imaging, PET/CT, MRI/PET/SPECT) molecular imaging, meaning that hybrid molecules (i.e. containing two imaging probes, such as iron oxide nanoparticles coupled with a fluorescent dye, or paramagnetic and fluorescent dendrimers, or paramagnetic and radioactive dendrimers, or paramagnetic and radioactive chelates) are synthesized to attain the high spatial resolution of an "anatomical" imaging method (such as MRI and CT) with the nanomolar detection limit of a "sensitive" imaging method (such as PET, SPECT, fluorescence imaging). This allows the quantification of beta cell mass, and the precocious diagnosis of pancreas adenocarcinoma.

The imaging probe according to the invention (at least one peptide molecule bound to a contrast agent) is used to perform in vitro kinetic assays aiming to investigate the modulation of $Na^+/K^+$-ATPase activity in the presence of FXYD2-gamma-a. The imaging probes act by themselves as modulators of $Na^+/K^+$-ATPase, subsequent to the interaction with FXYD2-gamma-a. The location of the imaging probes in the cell membranes is visualized by electron microscopy or by fluorescent microscopy depending on their chemical composition. This allows the investigation of the location of the $Na^+/K^+$-ATPase in the cell membrane of beta cells or of other related cells.

The pharmacokinetic parameters (elimination half-life, clearance, volume of distribution) and the biodistribution profile are investigated in the animal models. In addition to the classical methods, the biodistribution of the imaging probes in various organs is investigated by histological techniques, the compounds bound to the cell membranes being detected by fluorescence or by the PEG moiety or by an anti-PEG antibody. In this context, the imaging probes are used to certify the expression or the absence of expression of FXYD2-gamma-a in various organs.

The invention therefore provides a non-invasive method for the diagnosis or prognosis of a diabetic disorder such as type 1 or type 2 diabetes mellitus (T1D or T2D) or hyperinsulinemia, by detecting and/or measuring the beta cell mass of a subject and comparing it to a reference amount of beta cell mass of a healthy subject. An increase of the beta cell mass in the subject under investigation points to a condition of hyperinsulinemia, while a reduction of the beta cell mass in the subject under investigation points to a condition of diabetes mellitus of type 1 or 2.

The non-invasive method for the diagnosis or prognosis of a diabetic disorder encompasses the highly specific detection and/or visualization of beta cells through the detection of the beta cell-specific biomarker FXYD2-gamma-a. The detection of the specific marker is done by using a labeled, such as but not limited to radioisotopically labeled, peptide molecules that bind the biomarker with high specificity. These peptide molecules are provided by the present invention.

In another embodiment, the present invention provides a method of in vivo diagnosing a beta-cell-related disorder comprising the following steps: a) introducing into a subject the peptide molecules of the present invention, wherein said peptide molecules are isotopically labeled, b) the in vivo visualization of the peptide molecules specifically binding to the beta cell population in the pancreas using PET, PET-CT or SPECT or MRI, c) quantifying the beta cells mass in said subject, d) comparing of the beta cell mass data obtained in step c) with the beta cell mass of a healthy subject, or of a previous analysis of the same subject, e) diagnosing the subject as having diabetes or being at risk of having diabetes when the level of beta cell mass obtained in step c) is reduced as compared to that of a healthy subject and diagnosing the subject as having hyperinsulinemia or being at risk of having hyperinsulinemia when the level of beta cell mass obtained in step c) is increased as compared to that of a healthy subject, or of a previous analysis of the same subject.

In one embodiment, the diagnostic or prognostic method of the invention uses Positron Emission Tomography (PET), a nuclear medicine medical imaging technique which produces a three-dimensional image or map of functional processes in the body. The system detects pairs of gamma rays emitted indirectly by a positron-emitting radioisotope, which is introduced into the body through radioisotipically labeled peptide molecules of the present invention. Labeled peptide molecules in the body are then reconstructed by computer analysis. In modern scanners, a PET scan is combined with a CT X-ray scan (PET-CT) performed on the patient at the same time, in the same machine, providing the structural reference of the organs etc. In an alternative embodiment, single photon emission computed tomography (SPECT) imaging can be used in the diagnostic or prognostic method of the invention. SPECT uses a gamma camera to acquire multiple 2-D projections from multiple angles. A computer is then used to apply a tomographic reconstruction algorithm to the multiple projections, yielding a 3-D dataset. This dataset may then be manipulated to show thin slices along any chosen axis of the body. The same technique of analysis can also be applied for MRI images.

Labels used in PET or PET-CT are short-lived radioisotopes such as carbon-11 (~20 min), nitrogen-13 (~10 min), oxygen-15 (~2 min), and fluorine-18 (~110 min) or medium-lived radioisotopes such as iodine-124 (~4 days) when appropriate.

In another embodiment, the peptide molecules of the present invention are used in the preparation of a diagnostic composition for the in vitro and in-vivo diagnosis of pancreatic beta-cell related disorders.

The method of in vivo diagnosis or prognosis can be used to diagnose insulin-related disorders such as type 1 or type 2 diabetes mellitus, hyperinsulinemia and pancreatic cancer derived from the beta cells.

In another embodiment, the peptide molecules of the present invention are used in various in vitro immunochemical systems of reaction and detection. They are either immobilized on a surface and used to capture the FXYD2-gamma-a or cells of interest, or they can be labeled with a reporter tag that can be detected by spectrophotometry, fluorescence, phosphorimaging, surface plasmon resonance, or MALDI-TOF (matrix associated laser desorption ionization time-of-flight) mass spectrometry. For in vitro diagnostic applications, they are used to identify cancer cells in tumor biopsies from patients with pancreas adenocarcinoma.

In another embodiment, the peptide molecules of the present invention are used in the targeting of other molecules to the pancreas, more precisely to the pancreatic beta cells.

In another embodiment, the invention provides a method for targeting molecules to the pancreas, more precisely to the pancreatic beta cells, comprising the steps of: binding said molecule to the peptide molecules of the present invention b) introducing said molecule bound to the peptide molecules into a subject. Molecules targeted towards the beta cells or cancer cells can be, but are not limited to, treatment molecules. Thus, the inherent secondary systemic effects are limited.

In another embodiment, the present invention provides a kit for specifically measuring beta cell-mass, and/or for diagnosing a beta-cell-related disorder, and/or for purifying beta cells in a subject comprising at least the labeled peptide molecules described herein.

For treating insulin-related disorders, pancreatic islet transplantation is an option. Typically, the Edmonton protocol is applied wherein specialized enzymes are used to remove islets from the pancreas of a deceased donor. Because the islets are fragile, transplantation occurs soon after they are removed. Typically a patient receives at least 10,000 islet "equivalents" per kilogram of body weight, extracted from two donor pancreases. Patients often require two transplants to achieve insulin independence. Some transplants have used fewer islet equivalents taken from a single donated pancreas. Transplants are often performed by a radiologist, who uses x rays and ultrasound to guide placement of a catheter through the upper abdomen and into the portal vein of the liver. The islets are then infused slowly through the catheter into the liver. The patient receives a local anesthetic and a sedative. In some cases, a surgeon may perform the transplant through a small incision, using general anesthesia.

The key of success for such a beta cell transplantation treatment is of course the purity of the beta cell preparation used for the transplantation. The invention provides for methods of specifically isolating beta cells for use in islet transplantation and tools for follow up of transplanted beta cells.

In a further embodiment, the invention provides for methods to isolate and/or purify pancreatic beta cells from pancreatic tissue, by visualizing or labeling the beta cells in a specific manner using peptide molecules that specifically bind the FXYD2-gamma-a biomarker.

In a further embodiment, the invention provides a method for following up the success of the transplantation of beta cells in a subject comprising the following steps of: a) measuring the pancreatic beta-cell mass in the subject in a certain period of time after transplantation of the subject with beta cells, b) determining the success of the transplantation by comparing the beta cell mass in the course of time.

In another embodiment, the invention provides a method for purifying or isolating beta cells from other pancreatic non-beta cells comprising the following steps: a) tagging the beta cells with the peptide molecules, wherein said peptide molecules are labeled, b) isolating the labeled cells from the non-labeled cells through the tag on the beta cells, thereby obtaining a substantially pure beta cell preparation.

In another embodiment, the invention provides a method for identification of regeneration of beta cells comprising the steps of: a) tagging the beta cells with the peptide molecules, wherein said peptide molecules are labeled, b) isolating the labeled cells from the non-labeled cells through the tag on the beta cells, thereby obtaining a substantially pure regenerated beta cell preparation, c) performing immunohistochemistry to identify the number of newly regenerated beta cells and to define the new beta cell mass, d) follow up of therapeutic strategies and detect beta cell mass recovery.

The peptide molecules of the present invention are used to certify the beta cells derived from other sources than pancreatic islets i.e. embryonic stem cells, pancreatic progenitor cells in the ductal epithelium, alpha cells, hepatocytes, exocrine cells in pancreatic acini, before using them in human transplantation. This can be accomplished by immunocytochemistry methods, the peptide being involved as a specific biomarker.

In another embodiment, the invention provides a method for identification of stem cell populations in order to derive functional insulin-expressing cells comprising the following steps: a) tagging the treated stem cells with a labeled peptide molecule of the present invention, b) isolating the labeled cells from the non-labeled cells through the tag on the potential beta stem cells, thereby obtaining a substantially pure beta stem cell preparation. The method of the invention can in certain embodiments further comprise the steps of: c) performing immunohistochemistry to identify the number of beta stem cells, and to define the new beta cell mass and d) follow up of therapeutic strategies and detect newly formed beta cell mass.

The above separation methods can for example be performed by separating labeled cells from non-labeled cells using standard separation techniques based on the retention of labeled peptide molecules of the present invention that specifically bind the FXYD2-gamma-a subunit.

One option is to use the peptide molecules of the present invention with a small magnetic particle or magnetic bead. The bead-binding molecule conjugate is then directed to the beta-cells in the pancreatic cell preparation and the beta cells can be specifically purified from the total pancreatic cell preparation by using e.g. an electromagnetic field. In some systems, the sample is processed through a column that generates a magnetic field when placed within the separator instrument, retaining only the labeled cells.

Other systems offer simplified versions of the magnetic separator. Instead of a column and separator instrument, these systems use a simple magnet to directly retain the labeled cells within the tube, while the supernatant is drawn off. Some of these systems can be used in a positive or negative selection manner. Negative or enrichment selection means that unwanted cells can be labeled (captured), leaving the cells of interest label-free. The magnetic particles do not interfere with flow cytometry, nor do they interfere with cell growth, according to Hammonds, so cells that have been isolated using such a system can be further cultured.

Magnetic separation has proven uniquely powerful and broadly applicable, sometimes leading to 70% recovery of the target cells and up to 98% purity while retaining cell viability.

The term "label" includes all suitable isotopic labels for use in PET, PET-CT or SPECT analysis, labels suitable for specific extraction such as magnetic or paramagnetic beads, labels suitable for diagnosis in vitro such as fluorescent dyes or other luminescent labels, known in the art.

The term "beta cell related disorder" described in the methods or uses or kits of the invention encompasses all disorders related to beta cells such as: type 1 diabetes mellitus, type 2 diabetes mellitus, hyperinsulinemia, obesity, neuroendocrine tumors or occurrence of insulinoma.

Additionally, the peptide molecules of the invention can also be used in in-vitro methods for the analysis of the amount or characteristics of beta cells in a cell culture, either obtained from a biopsy or from a cell-line derived culture. Peptide molecules of the invention can further be used to characterize the differentiation state of cells such as modified stem cells, differentiated in vitro as beta cells.

EXAMPLES

The invention is illustrated by the following non-limiting examples

Example 1

Screening for Peptides Binding the FXYD2-Gamma-a Subunit

Commercially available peptide libraries were screened and peptides binding the FXYD2-gamma-a subunit were retained for further analysis. The FXYD2-gamma-a is a regulating subunit of the Na—K-ATPase that contains 66 amino acids, from which 11 are specific to human beta-cells (Flamez D et al. DOI 10.1007/s00125-010-1714-z). Commercially available linear heptapeptide libraries were screened via M13 phage display methodology. After 4 screening rounds, 42 clones were selected for further characterization: sequencing and dissociation constant ($K_d$) determination. The selected clone had a $K_d$ of $9.3 \times 10^{-9}$ M and carried 2 peptides. The latter were synthetized either separately (called P89 and P90) or fused via a short sequence of the pill protein (called P88). All three synthetized peptides were further tested. P88 and P89 had a $K_d$ of $1.89 \times 10^{-6}$ M and $1.09 \times 10^{-4}$ M respectively while the $K_d$ of P90 could not be determined. The sequences of the peptides are:

P88:    LPLSRHYGGGSVPFYSHSNTHHTSM (SEQ ID NO: 2)

P89:    LPLSRHY (SEQ ID NO: 5)

P90:    NTHHTSM (SEQ ID NO: 6)

PHI:    GGGSVPFYSHS (SEQ ID NO: 7)

A BLAST search revealed that 14 amino acids of P88 have homology to the sodium channel protein type 10 subunit alpha (Q9Y5Y9). Other biochemical parameters of P88, summarized in table 1, were theoretically determined using the proteomics server ExPASy and the MarvinSketch 5.2.0 software.

TABLE 1

| theoretically determined P88 biochemical parameters | |
|---|---|
| Parameter | P88 |
| Half life time | 5.5 hours |
| Isoelectric point | 8.62 |
| Partition coefficient of the ionic species | −18.0 |
| Partition coefficient of the nonionic species | −6.2 |
| LogD | −12.2 |
| Grand average of hydropathicity (GRAVY) | −0.668 |
| Aliphatic index | 42.80 |

Example 2

P88 High Interaction with CAPAN2 Cells Compared to PANC1 Cells

The specificity of P88, P89, P90 and a polyclonal antibody against the N-terminal sequence of FXYD2-gamma-a protein to the FXYD2-gamma-a regulatory subunit expressed by CAPAN-2 cells was checked by immunocytochemistry and immunofluorescence tests.

Immunocytochemistry tests were performed using the biotinylated peptides. An anti-biotine antibody was used and was recognized by a secondary antibody coupled to the peroxidase. The polyclonal antibody against the N-terminal sequence of FXYD2-gamma-a protein to the FXYD2-gamma-a was detected using a secondary biotinylated antibody that fixes a complex containing streptavidin, biotin and peroxidase. The latter gives a brown color in the presence of 3,3'-diaminobenzidine (DAB).

Figure 2:
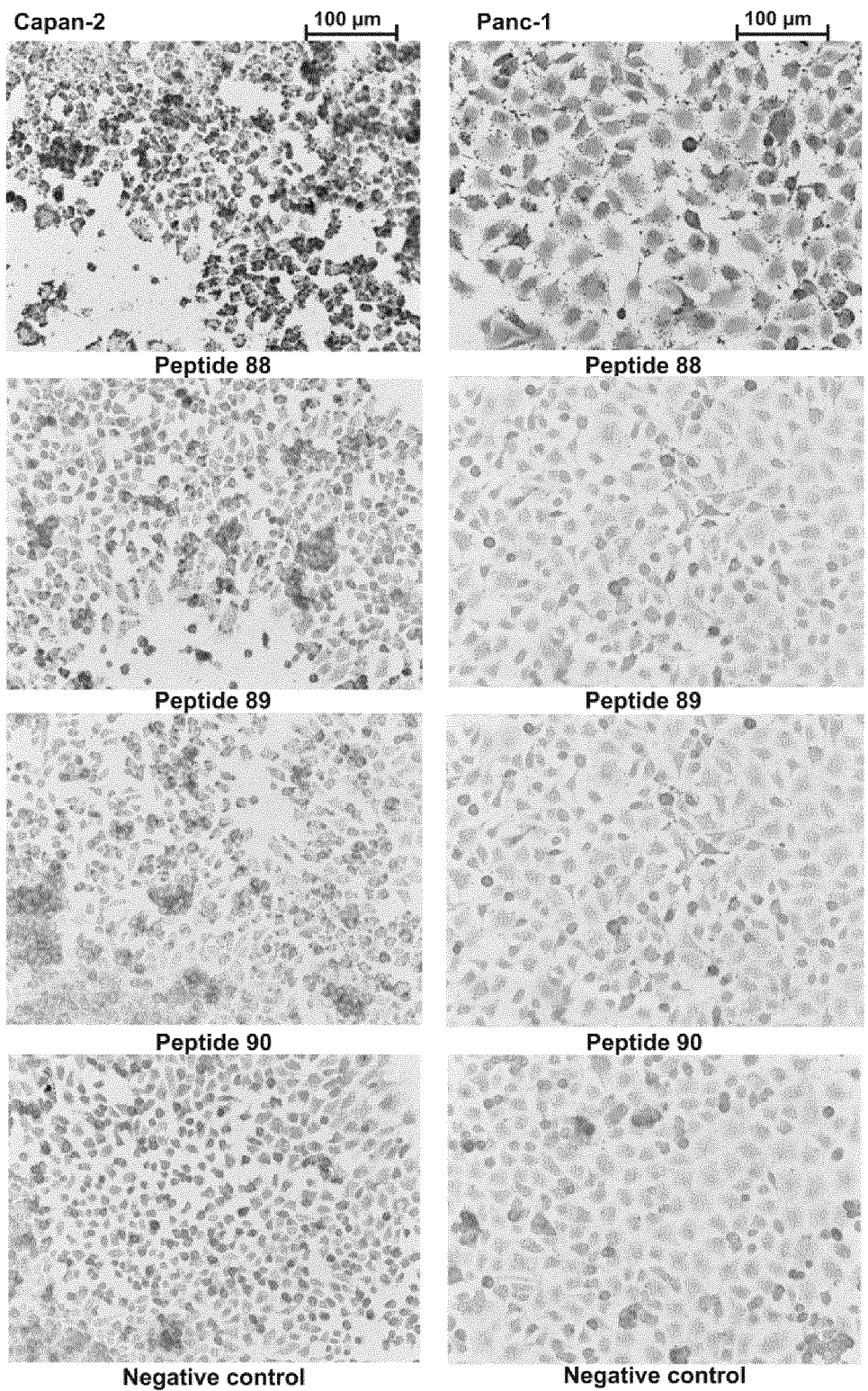
FIG. 2 Immunocytochemistry test performed on CAPAN2 cells (left panel) and PANC1 cells (right panel) using peptides P88, P89 and P90. The lowest line shows the negative control samples.

The tests reproducibly (3 times) showed that the interaction of P88 with the pancreatic beta cells is more specific compared to the polyclonal antibody against the N-terminal sequence of FXYD2-gamma-a. Indeed, a brown color was obtained with both CAPAN2 cells and PANC1 cells when the polyclonal antibody was used while the brown coloration was more localized in the CAPAN2 cells when P88 was used (FIGS. 1 and 2). The interaction of P89 and P90 with CAPAN2 cells was less specific compared to P88 (FIG. 2).

These results were confirmed by immunofluorescence. Each secondary antibody described above was coupled to a fluorophore such as fluorescein which gives a green color at a certain wavelength. DAPI (4',6-diamidino-2-phenylindole) was also used in order to stain the cell nuclei in blue. This allowed us to compare the localization of the blue and the green coloration. The results showed that in CAPAN 2 cells, the green fluorescence pattern obtained using P88 was correspondent to the blue fluorescent pattern of DAPI. In PANC1 cells, few green fluorescent spots were obtained (results not shown). Therefore, P88 interacts specifically with CAPAN2 cells and is thus specific to the FXYD2-gamma-a biomarker. When the polyclonal antibody against the N-terminal sequence of FXYD2-gamma-a was used, the green fluorescence obtained in PANC1 cells was less intense than the one obtained in CAPAN2 cells but it was more abundant compared to the use of P88 in PANC1 cells (results not shown). This indicates that P88 is more specific to pancreatic beta cells than the anti-FXYD2-gamma-a polyclonal antibody.

The images obtained by immunofluorescence test were analyzed using ImageJ software in order to semi-quantitatively evaluate the fluorescent labeling. The following equation was used to calculate the relative rate of fluorescent labeling (RRFL):

$$RRFL = (SI_{sample}/N_{cells})/(SI_{blanc}/N_{cells})$$

Wherein SI is the signal intensity, N is the number of cells and blanc is the negative control sample. The results are showed in FIG. 3 A.

Figure 3:
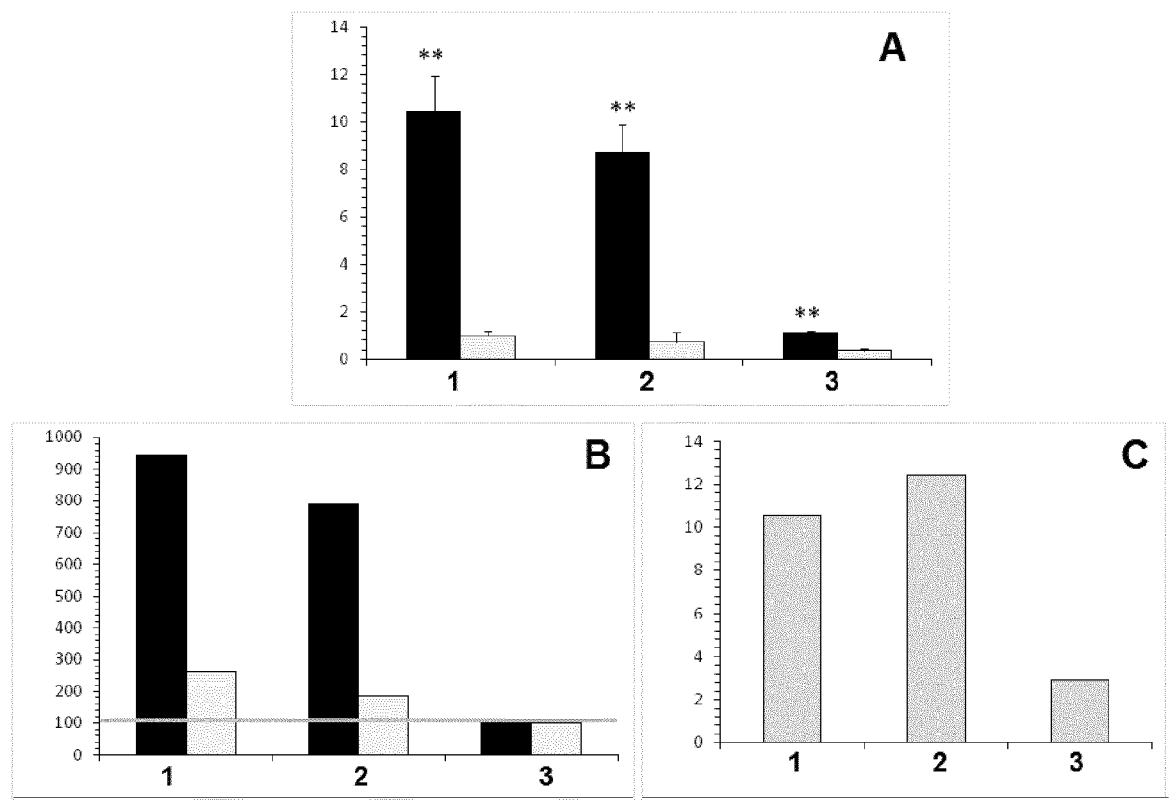
FIG. 3 ImageJ semi-quantitative analysis of microscopic images obtained from the immunofluorescent labeling of CAPAN2 (black columns) and PANC1 cells (white columns). A shows the relative rate of immunofluorescence labeling (RRFL). B shows the percentage of RRFL obtained when P88 was used at two different concentrations (5 μM and 10 μM) which was determined in comparison to the RRFL obtained when the anti-FXYD2-gamma-a polyclonal antibody was used. C shows the ratio between the RRFL measured in CAPAN2 cells and the RRFL measured in PANC1 cells. For A, B and C, 1: 10 μM of P88 was used, 2: 5 μM of P88 was used, 3: 5 μg of anti FXYD2-gamma-a antibody was used and * *=p<0.01.

The percentage of RRFL obtained when P88 was used at two different concentrations (5 μM and 10 μM) was determined compared to the RRFL obtained when the polyclonal antibody against the N-terminal sequence of FXYD2-gamma-a was used (FIG. 3 B). The ratio between the RRFL measured in CAPAN2 cells and the RRFL measured in PANC1 cells was also determined (FIG. 3 C). The RRFL produced by P88 (used at 10 μM) in CAPAN2 cells is 945% higher than the RRFL produced by the anti-FXYD2-gamma-a polyclonal antibody and 791% higher when the concentration of P88 was 5 μM. The ratio CAPAN2/PANC1 confirmed the labeling specificity of P88 compared to the used polyclonal antibody.

Example 3

P88 Specifically Interacts with Human Pancreatic Beta Cells

A co-localization of peptide P88, insulin and glucagon was performed on human pancreatic histological sections using immunohistochemistry and immunofluorescence tests. Insulin is a hormone produced by the beta cells of Langerhans islets while glucagon is produced by the alpha cells of the same islets.

Figure 4:
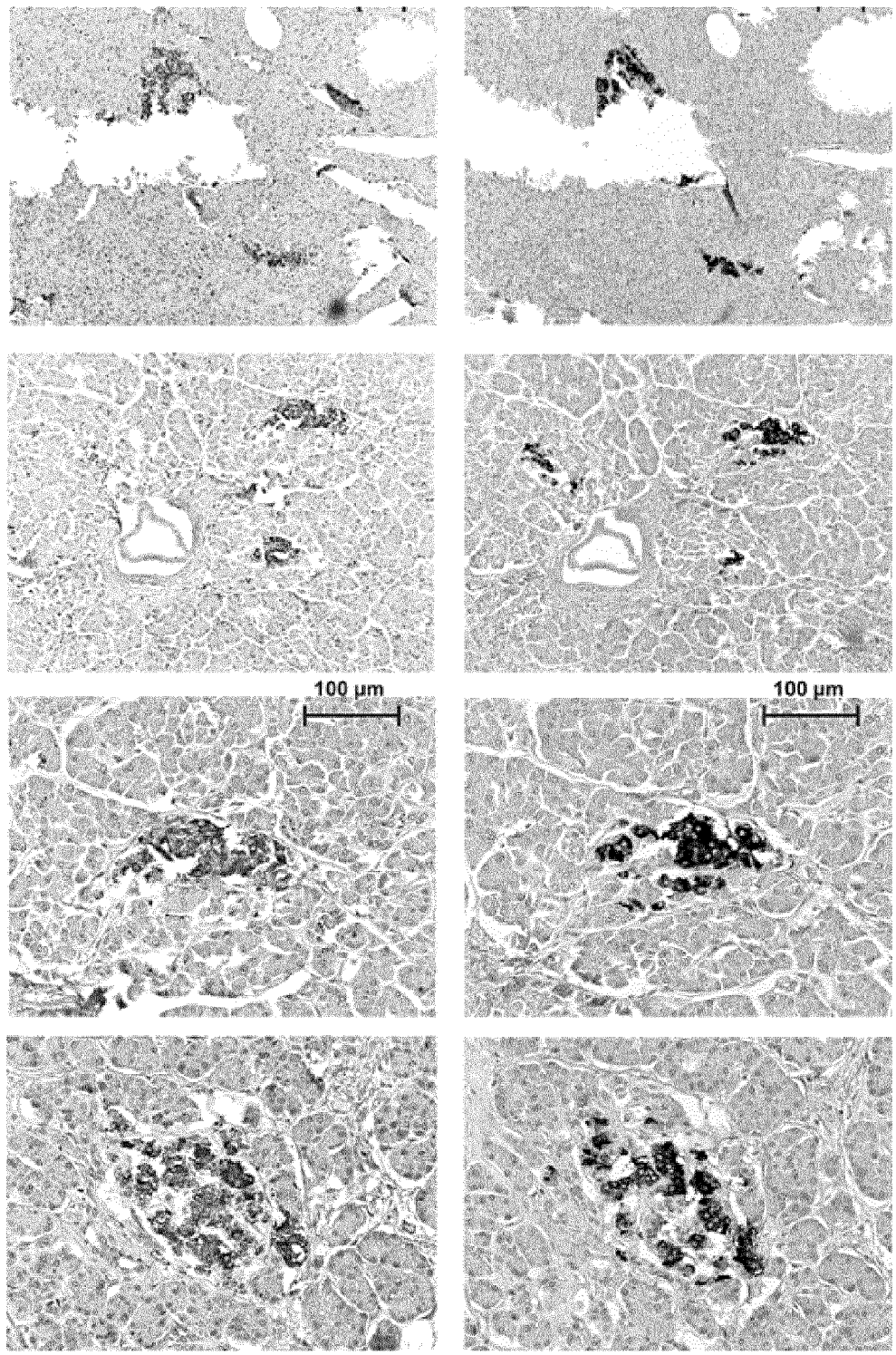
FIG. 4 Immunohistochemistry test of human pancreatic Langerhans islets using P88 (left panel) and anti-insulin antibody (right panel).

Immunohistochemistry tests clearly showed that a high specific marking of the pancreatic Langerhans islets is obtained when using the P88. The marking is the same as the one obtained when the antibody anti-insulin was used (FIG. 4).

Figure 5:
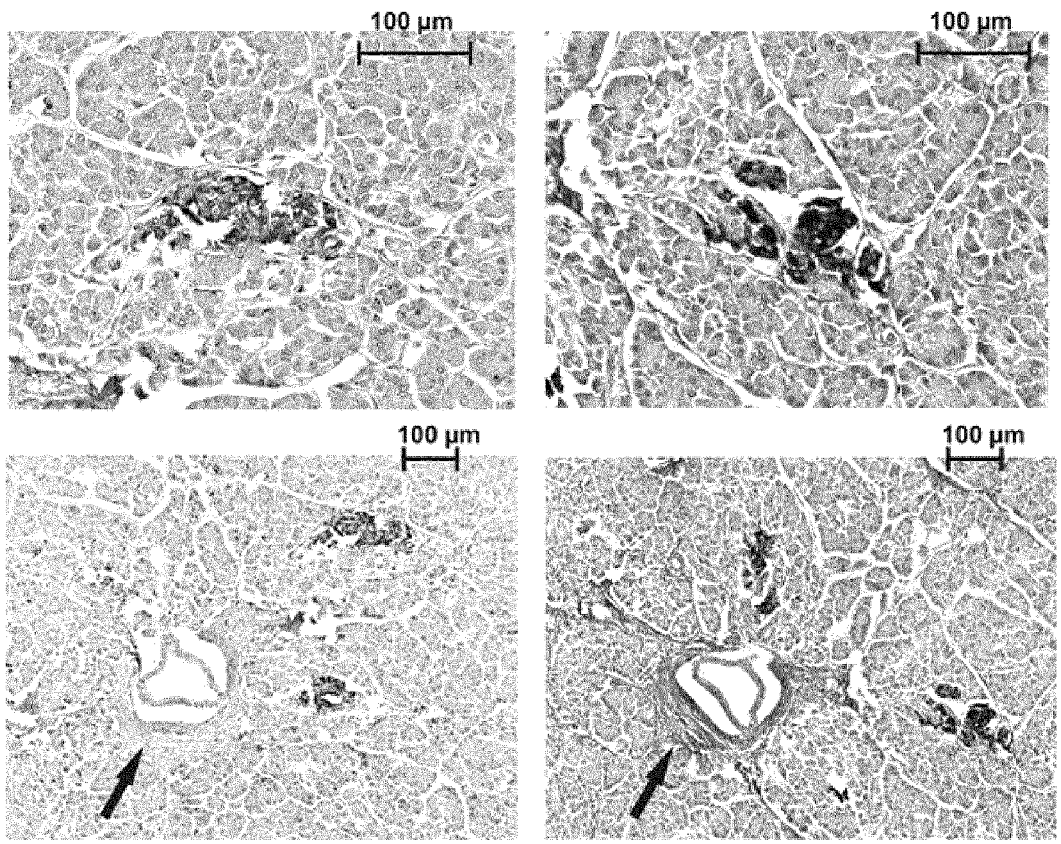
FIG. 5 Immunohistochemistry test of human pancreatic Langerhans islets using P88 (left panel) and a polyclonal antibody against the N-terminal sequence of FXYD2-gamma-a (right panel). The arrows in the lower images show that the anti-FXYD2-gamma-a polyclonal antibody interacts with other structures of the pancreas than the beta cells which is not the case for P88.

In other immunohistochemistry tests, the anti-FXYD2-gamma-a polyclonal antibody was used. The results showed that the used polyclonal antibody interacts with other structures than the beta cells of the pancreas, which is not the case of the P88 peptide (FIG. 5). Therefore, P88 is highly specific to the pancreatic beta cells FXYD2-gamma-a biomarker.

Figure 10:
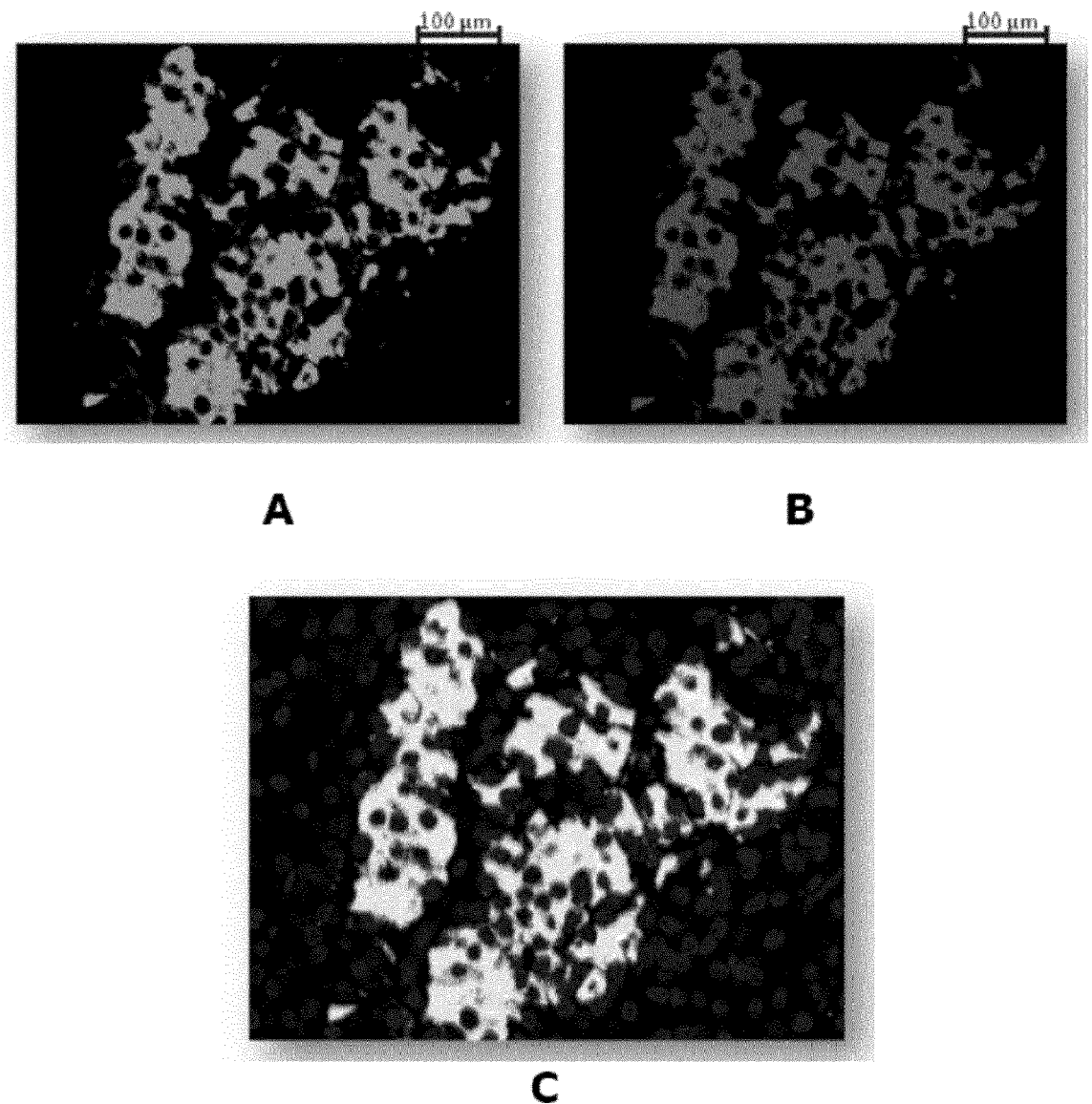
FIG. 10 Immunofluorescence co-localization tests performed on human pancreatic histological sections. A P88 was used, B anti-insulin antibody was used, C obtained image after merging A and B.
Figure 11:
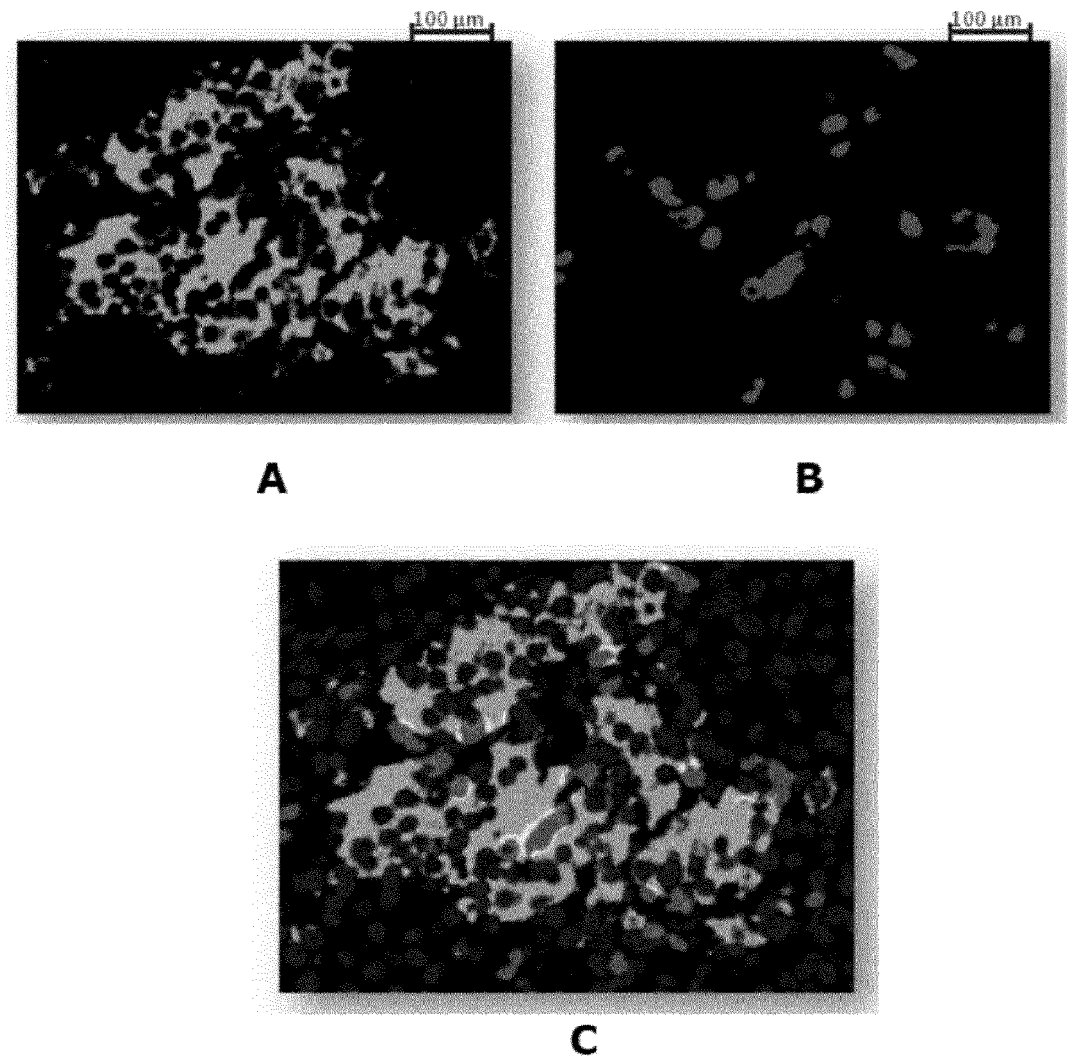
FIG. 11 Immunofluorescence co-localization tests performed on human pancreatic histological sections. A P88 was used, B anti-glucagon antibody was used, C obtained image after merging A and B.

Immunofluorescence tests were performed on human pancreatic histological sections such as P88 was detected together with insulin or glucagon. In another test, insulin was detected together with the polyclonal antibody against the N-terminal sequence of FXYD2-gamma-a. Insulin (specific of beta cells) was detected with a primary anti-insulin antibody which was detected using a secondary antibody coupled to Texas Red. Glucagon was detected with a primary anti-glucagon antibody which was also detected using a secondary antibody coupled to Texas Red. The latter gives red color to the antigenic sites. Biotinylated P88 was detected using a primary antibody anti-biotin and a secondary antibody coupled to fluorescein. The polyclonal antibody against the N-terminal sequence of FXYD2-gamma-a was also detected using a secondary antibody coupled to fluorescein. Antigenic sites marked by fluorescein are visualized in green color. DAPI was also used in order to stain the cells nuclei in blue. Pictures obtained with each staining (red, green and blue) were superimposed. A perfect co-localization of P88 and the anti-insulin antibody was obtained (illustrated by the obtained yellow color) as shown in FIG. 10, wherein in A P88 was used, in B the anti-insulin antibody was used and C is the obtained image after merging A and B. P88 and glucagon did not co-localize, as shown in FIG. 11, wherein in A P88 was used, in B the anti-glucagon antibody was used and C shows the obtained image after merging A and B.

Figure 12:
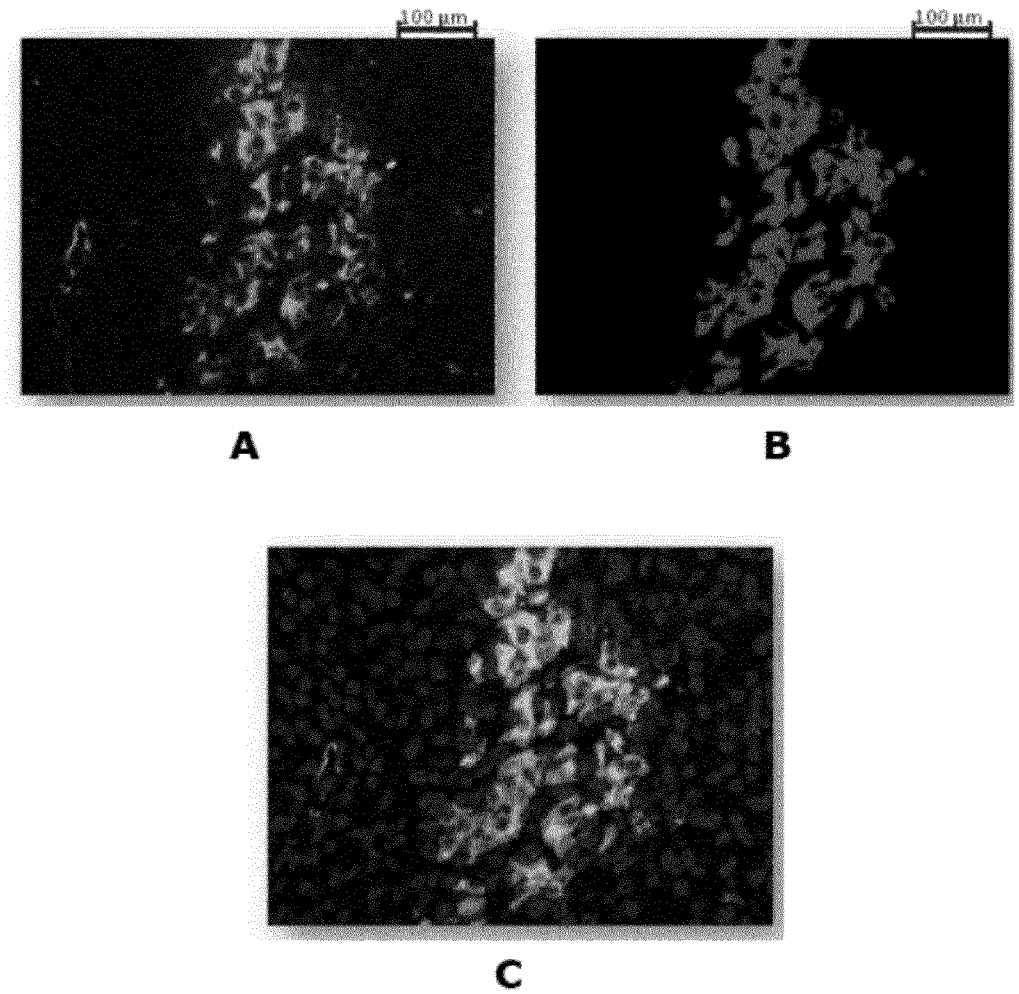
FIG. 12 Immunofluorescence co-localization tests performed on human pancreatic histological sections. A a polyclonal antibody against the N-terminal sequence of FXYD2-gamma-a protein was used, B anti-insulin antibody was used, C obtained image after merging A and B.

The results also showed that the antibody directed against the N-terminal sequence of FXYD2-gamma-a interacts with the beta cells. However, the co-localization between the insulin and the used antibody was less specific compared to the one showed for P88 and insulin. This is shown in FIG. 12, wherein in A the polyclonal antibody against the N-terminal sequence of FXYD2-gamma-a protein was used, in B the anti-insulin antibody was used and C shows the obtained image after merging A and B. These results confirm those obtained by immunohistochemistry test showing that P88 is specific to pancreatic beta cells and does not interact with the alpha cells or any other structure of the pancreas as it is the case for the FXYD2-gamma-a polyclonal antibody.

Example 4

P88 Coupled with Either USPIO or Carboxy Silane Coated Iron Oxide Nanoparticles Interact with CAPAN2 Cells CAPAN2 cells were labeled with USPIO nanoparticles coupled to P88 or with carboxy silane coated iron oxide nanoparticles coupled to P88. USPIO-polyethylene glycol (PEG) were used as negative contrast agent. Labeled cells were visualized by MRI and the concentration of contrast agents bound to the cells was determined by iron dosage.

CAPAN2 cells were used with different concentrations ranging from $2 \times 10^6$ cell per 100 μl to $0.1 \times 10^6$ cells per 100 μl corresponding respectively to the beta cell concentration in healthy pancreas and in a pancreas with diabetes. MRI showed a clear labeling of the CAPAN2 cells when USPIO-P88 and silane coated iron oxide nanoparticles-P88 were used. The labeling was also clearly observed with the lowest CAPAN2 cell concentration.

Figure 6:
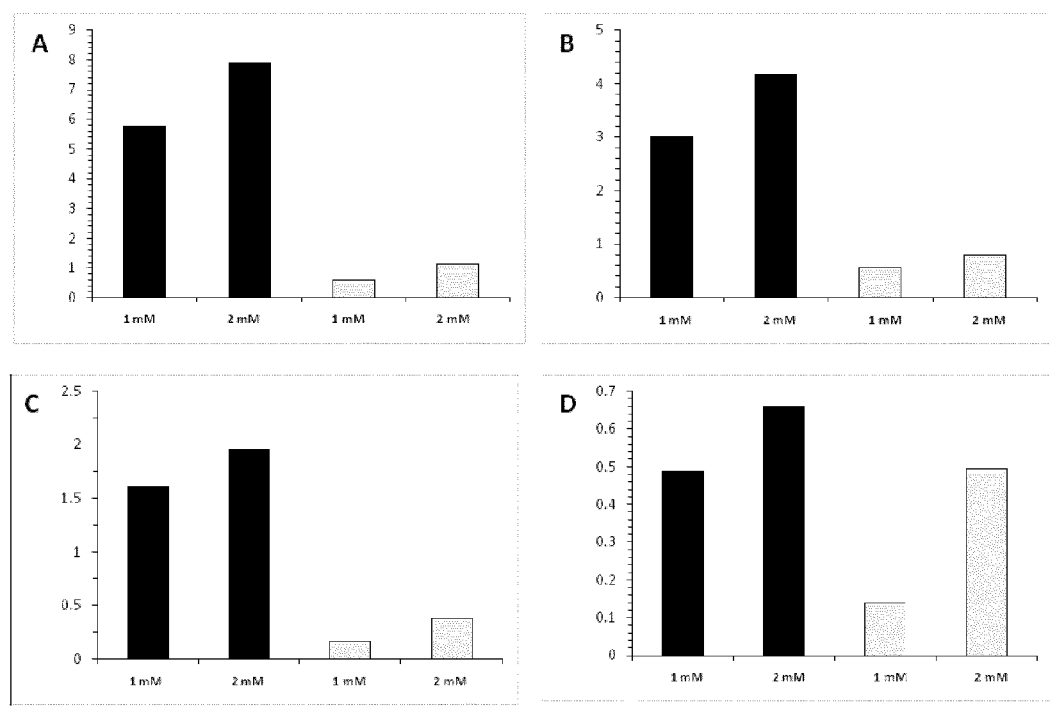
FIG. 6 Transverse relaxation rates (y axis) of CAPAN2 cells labeled with either USPIO-P88 (black columns) or with USPIO-PEG (white columns). A concentration of CAPAN2 cells is $2\times10^6$ cell/100 μl, B concentration of CAPAN2 cells is $1\times10^6$ cell/100 μl, C concentration of CAPAN2 cells is $0.5\times10^6$ cell/100 μl and D concentration of CAPAN2 cells is $0.1\times10^6$ cell/100 μl.

MRI measurements of the same cellular samples showed that the transverse relaxation rates of CAPAN2 cells labeled with either USPIO-P88 (FIG. 6) or silane coated iron oxide nanoparticles-P88 (results not shown) were higher than the transverse relaxation rates of CAPAN2 cells labeled with USPIO-PEG. This result was independent from the concentration of CAPAN2 cells.

Figure 7:
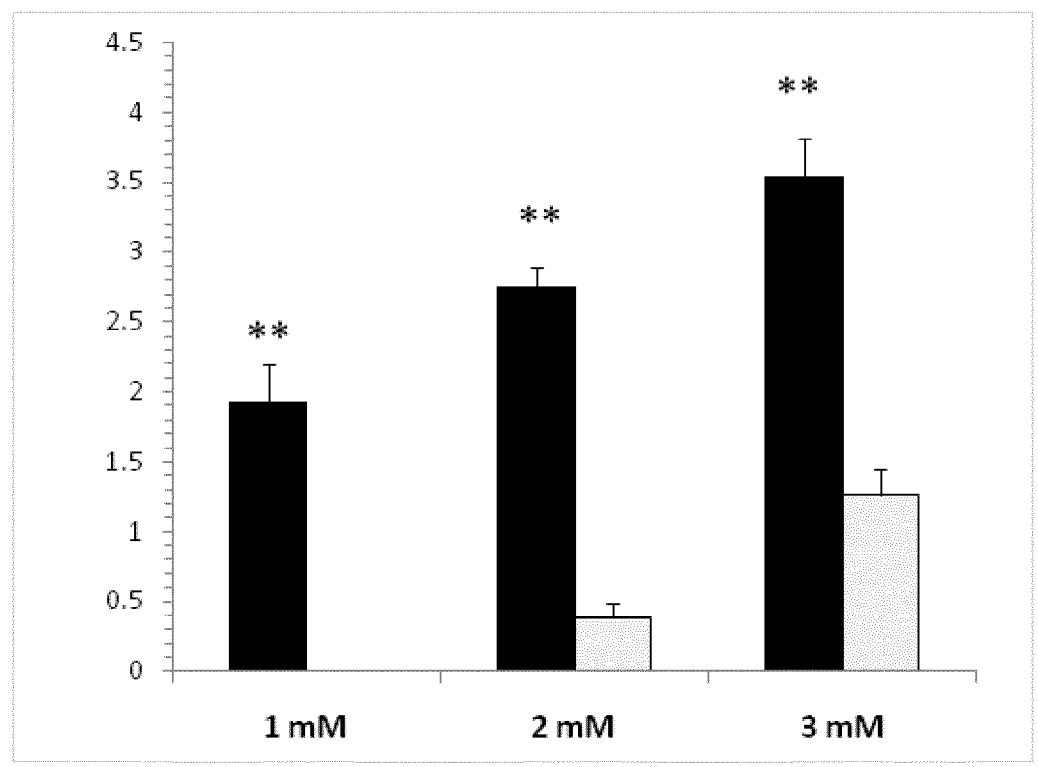
FIG. 7 Iron concentration (y axis) of CAPAN2 cells labeled with different concentrations (x axis) of USPIO-P88 (black columns) and USPIO-PEG (white columns). * *=p<0.01

Iron dosage of CAPAN2 cells labeled with different concentrations of contrast agent USPIO-P88 or silane coated iron oxide nanoparticles-P88 (1 mM, 2 mM and 3 mM) revealed that the amount of iron captured by the CAPAN2 cells is always higher with these contrast agents compared to USPIO-PEG contrast agent (FIG. 7). This confirms the specificity of P88 to the pancreatic beta cells biomarker FXYD2-gamma-a and the efficacy of using the P88 coupled to a contrast agent in MRI.

Example 5

Figure 8:
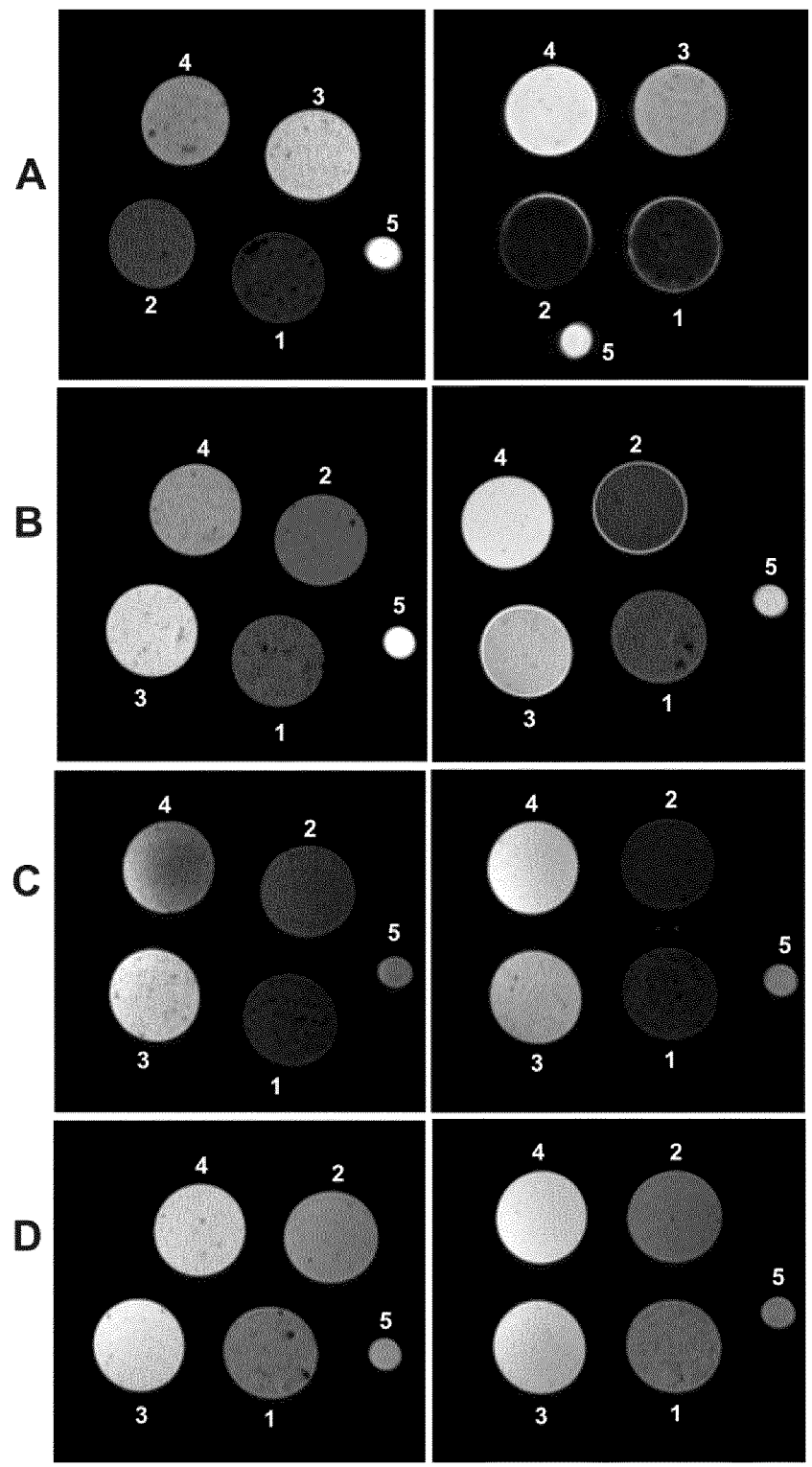
FIG. 8 MRI visualization of human Langerhans islets labeled with either USPIO-P88 or with USPIO-PEG. A 1250 Langerhans islets/100 μl are used ($2.5\times10^6$ cell/100 μl), B 625 Langerhans islets/100 μl are used ($1.25\times10^6$ cell/100 μl), C 312 Langerhans islets/100 μl are used ($0.625\times10^6$ cell/100 μl) and D 156 Langerhans islets/100 μl are used ($0.312\times10^6$ cell/100 μl). Left panel and right panel are 2 different series of samples. 1 pure islets labeled with USPIO-P88, 2 less pure islets labeled with USPIO-P88, 3 pure islets labeled with USPIO-PEG, 4 less pure islets labeled with USPIO-PEG, 5 gelatin.

P88 Coupled with Either USPIO or Carboxy Silane Coated Iron Oxide Nanoparticles Interact with Pancreatic Human Langerhans Islets Contrast agents USPIO and carboxy silane coated iron oxide nanoparticles coupled to the peptide P88 were tested for their interaction with the human Langerhans islets and compared to the use of USPIO-PEG contrast agent. FIG. 8 shows a clear difference between the labeling of the islets using USPIO-P88 and USPIO-PEG and points to the specificity of USPIO-P88 even at low concentration (FIGS. 8, C and D) and non-pure islet samples (FIG. 8, samples 1 and 2 compared to samples 3 and 4).

Figure 9:
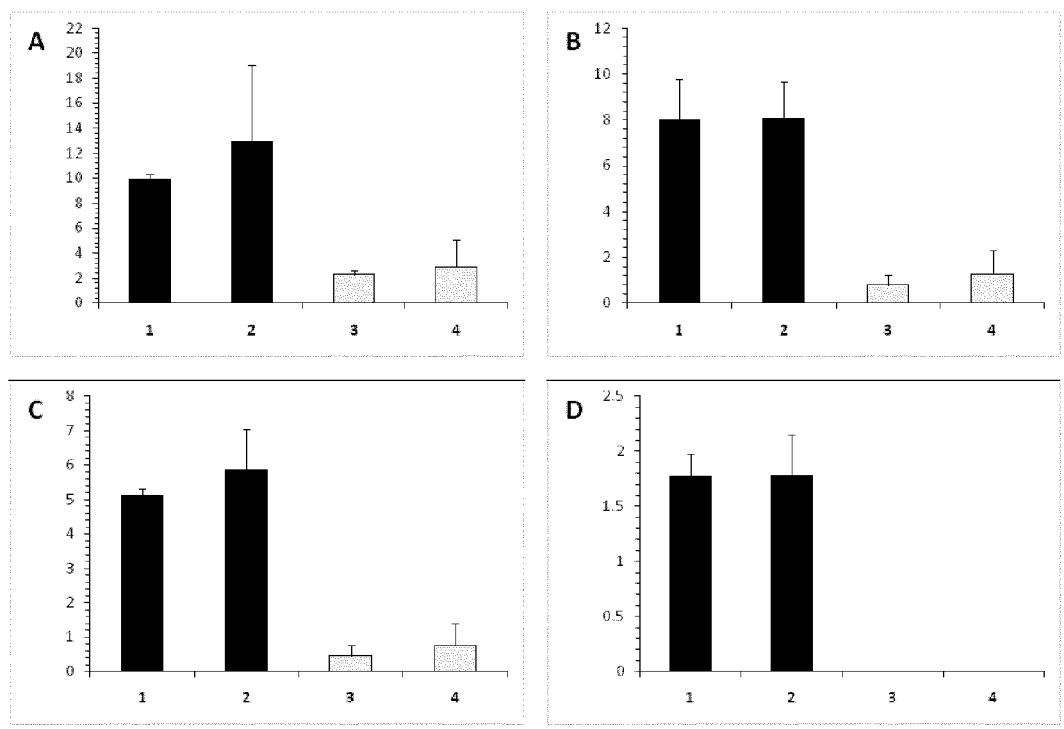
FIG. 9 Transverse relaxation rates (y axis) of human Langerhans islets labeled with either USPIO-P88 or with USPIO-PEG. A 1250 Langerhans islets/100 μl are used ($2.5\times10^6$ cell/100 μl), B 625 Langerhans islets/100 μl are used ($1.25\times10^6$ cell/100 μl), C 312 Langerhans islets/100 μl are used ($0.625\times10^6$ cell/100 μl) and D 156 Langerhans islets/100 μl are used ($0.312\times10^6$ cell/100 μl). 1 pure islets labeled with USPIO-P88, 2 less pure islets labeled with USPIO-P88, 3 pure islets labeled with USPIO-PEG, 4 less pure islets labeled with USPIO-PEG.

MRI measurements of the same cellular samples showed that the transverse relaxation rates of human Langerhans islets labeled with either USPIO-P88 (FIG. 9) or silane coated iron oxide nanoparticles-P88 (results not shown) were higher than the transverse relaxation rates of human Langerhans islets labeled with USPIO-PEG. This result was independent from the concentration and the purity of the used human Langerhans islets.

Example 6

P88 Coupled with Either USPIO or Carboxy Silane Coated Iron Oxide Nanoparticles are Specific to the Beta Cells of Langerhans Islets Co-localization tests were performed where antibodies anti-PEG were added to the Langrehans islets labeled with USPIO-P88 nanoparticles, the Langrehans islets labeled with carboxy silane coated iron oxide nanoparticles coupled to the peptide P88 and to the Langrehans islets labeled with USPIO-PEG. A secondary antibody that recognizes the anti-PEG antibody and coupled to the fluorescein was also used which created a green fluorescence.

Insulin was labeled with primary anti-insulin antibody and a secondary antibody coupled to Texas red which created a red fluorescence. After superposition of the different obtained images, the red fluorescence zone of the insulin perfectly co-localized with the green fluorescence zone of the Langerhans islets labeled with the USPIO-P88 and with the carboxy silane coated iron oxide nanoparticles coupled to P88 (observed by a yellow coloration—results not shown). This was not the case for the Langerhans islets labeled with USPIO-PEG, where no perfect match could be observed with the red fluorescence of the insulin. This shows again the specificity of the P88 to the pancreatic beta cells and the convenient use of the peptide molecule together with the contrast agents for MRI.

What is claimed is:

1. A synthetic peptide molecule that specifically binds the FXYD2-gamma-a isoform of pancreatic beta cells, wherein the peptide molecule comprises an amino acid sequence of:
   (a) X1-X2-X3-X4-X5-X6-X7-X8-X9-X10-X11-X12-X13-X14-X15-X16-X17-X18-X19-X20-X21-X22-X23-X24-X25 (SEQ ID NO: 1) and the functional equivalents thereof, wherein X1 is leucine or isoleucine, X2 is proline, X3 is leucine or isoleucine, X4 is serine or threonine, X5 is arginine, lysine or histidine, X6 is histidine, arginine or lysine, X7 is tyrosine, X8, X9 and X10 are glycine, X11 is serine or threonine, X12 is valine, leucine or isoleucine, X13 is proline, X14 is phenylalanine or leucine, X15 is tyrosine, X16 is serine or threonine, X17 is histidine, arginine or lysine, X18 is serine or threonine, X19 is asparagine or glutamine, X20 is threonine or serine, X21 and X22 are histidine, arginine or lysine, X23 is threonine or serine, X24 is serine or threonine, X25 is methionine or cysteine; or
   (b) X26-X27-X28-X29-X30-X31-X32-G-G-G-S-V-P-F-Y-S-H-S-X33-X34-X35-X36-X37-X38-X39 (SEQ ID NO: 3) and the functional equivalents thereof, wherein X26 is histidine arginine or lysine, X27 is aspartic acid or glutamic acid, X28 is arginine, lysine or histidine, X29 is leucine or isoleucine, X30 is lysine, arginine or histidine, X31 is serine or threonine, X32 is histidine, lysine or arginine, X33 is isoleucine or leucine, X34 is histidine, arginine or lysine, X35 is alanine, X36 is histidine, lysine or arginine, X37 is leucine or isoleucine, X38 is proline, X39 is glutamine or asparagine.

2. A method of labelling pancreatic beta cells comprising coupling at least one peptide molecule according to claim 1 to an iron oxide contrast agent.

3. The method according to claim 2, wherein said iron oxide contrast agent comprises a coating comprising at least a polysiloxane shell and at least one carboxylic acid group.

4. A method for measuring pancreatic beta-cell mass comprising the steps of:
   a) visualizing the beta cells in a sample using the peptide molecule according to claim 1, wherein said peptide molecule is labeled, and
   b) quantifying the amount of labeled beta cells.

5. A method of in vivo diagnosing a beta-cell-related disorder comprising the following steps:
   a) introducing into a subject the peptide molecule according to claim 1, wherein said peptide molecule is labeled,
   b) visualizing the peptide molecule specifically located to the beta cell population in the pancreas using PET, PET-CT or SPECT or MRI in vivo,
   c) quantifying the beta cells mass in said subject,
   d) comparing the beta cell mass data obtained in step c) with the beta cell mass of a healthy subject, or of a previous analysis of the same subject,
   e) diagnosing the subject as having diabetes or being at risk of having diabetes when the level of beta cell mass obtained in step c) is reduced as compared to that of a healthy subject and diagnosing the subject as having hyperinsulinemia or being at risk of having hyperinsulinemia when the level of beta cell mass obtained in step c) is increased as compared to that of a healthy subject, or of a previous analysis of the same subject.

6. A method for targeting molecules to the pancreas comprising the steps of:
   a) binding said molecule to the peptide molecule according to claim 1,
   b) introducing said molecule bound to the peptide molecule into a subject.

7. A kit for specifically measuring beta cell-mass, and/or for diagnosing a beta-cell-related disorder, and/or for purifying beta cells in a subject comprising at least the labeled peptide molecule according to claim 1.

8. A method for following up the success of the transplantation of beta cells in a subject comprising the following steps:
   a) measuring the pancreatic beta-cell mass in the subject in a certain period of time after transplantation of the subject with beta cells by the method of claim 4,
   b) determining the success of the transplantation by comparing the beta cell mass in the course of time.

9. A method for purifying or isolating beta cells from other pancreatic non-beta cells comprising the following steps:
   a) tagging the beta cells with the peptide molecule according to claim 1, wherein said peptide molecule is labeled,
   b) isolating the labeled cells from the non-labeled cells through the tag on the beta cells, thereby obtaining a substantially pure beta cell preparation.

10. The synthetic peptide molecule of claim 1, wherein the peptide amino acid sequence comprises LPLSRHYGGGSVPFYSHSNTHHTSM (SEQ ID NO: 2) or HDRLKSHGGGSVPFYSHSIHAHLPQ (SEQ ID NO: 4).

11. The synthetic peptide molecule of claim 1, wherein the peptide amino acid sequence comprises LPLSRHYGGGSVPFYSHSNTHHTSM (SEQ ID NO: 2).

12. The method of claim 2, further comprising specifically measuring pancreatic beta cell mass.

13. A method of carrying other molecules to the pancreas using at least one peptide molecule according to claim 1.

* * * * *

UNITED STATES PATENT AND TRADEMARK OFFICE
CERTIFICATE OF CORRECTION

| | | |
|---|---|---|
| PATENT NO. | : 8,981,053 B2 | Page 1 of 1 |
| APPLICATION NO. | : 14/125689 | |
| DATED | : March 17, 2015 | |
| INVENTOR(S) | : Robert Muller et al. | |

It is certified that error appears in the above-identified patent and that said Letters Patent is hereby corrected as shown below:

In the specification

In column 5 at line 55, Change "thereofl" to --thereof X1--.

In column 8 at line 24, Change "$p<0.01$" to --$p<0.01$.--.

In column 10 at line 41, Change "thereofl" to --thereof X1--.

In column 13 at line 12 (approx.), Change "radioisotipically" to --radioisotopically--.

In column 13 at lines 29-30 (approx.), Change "radioisoptopes" to --radioisotopes--.

In column 16 at line 22 (approx.), Change "PHI" to --pill--.

In the claims

In column 27 at line 1, In Claim 1, change "histidine" to --histidine,--.

Signed and Sealed this
Twenty-fourth Day of November, 2015

Michelle K. Lee
*Director of the United States Patent and Trademark Office*

SEQUENCE LISTING

```
<160> NUMBER OF SEQ ID NOS: 7

<210> SEQ ID NO 1
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa can be ile or leu
<220> FEATURE:
<221> NAME/KEY: VARIANT
<222> LOCATION: (2)..(2)
<223> OTHER INFORMATION: Xaa is pro
<220> FEATURE:
<221> NAME/KEY: VARIANT
<222> LOCATION: (3)..(3)
<223> OTHER INFORMATION: Xaa can be ile or leu
<220> FEATURE:
<221> NAME/KEY: VARIANT
<222> LOCATION: (4)..(4)
<223> OTHER INFORMATION: Xaa can be thr or ser
<220> FEATURE:
<221> NAME/KEY: VARIANT
<222> LOCATION: (5)..(5)
<223> OTHER INFORMATION: Xaa can be lys, his or arg
<220> FEATURE:
<221> NAME/KEY: VARIANT
<222> LOCATION: (6)..(6)
<223> OTHER INFORMATION: Xaa can be arg, his or lys
<220> FEATURE:
<221> NAME/KEY: VARIANT
<222> LOCATION: (7)..(7)
<223> OTHER INFORMATION: Xaa is tyr
```

-continued

```
<220> FEATURE:
<221> NAME/KEY: VARIANT
<222> LOCATION: (8)..(8)
<223> OTHER INFORMATION: Xaa is gly
<220> FEATURE:
<221> NAME/KEY: VARIANT
<222> LOCATION: (9)..(9)
<223> OTHER INFORMATION: Xaa is gly
<220> FEATURE:
<221> NAME/KEY: VARIANT
<222> LOCATION: (10)..(10)
<223> OTHER INFORMATION: Xaa is gly
<220> FEATURE:
<221> NAME/KEY: VARIANT
<222> LOCATION: (11)..(11)
<223> OTHER INFORMATION: Xaa can be thr or ser
<220> FEATURE:
<221> NAME/KEY: VARIANT
<222> LOCATION: (12)..(12)
<223> OTHER INFORMATION: Xaa can be leu, ile or val
<220> FEATURE:
<221> NAME/KEY: VARIANT
<222> LOCATION: (13)..(13)
<223> OTHER INFORMATION: Xaa is pro
<220> FEATURE:
<221> NAME/KEY: VARIANT
<222> LOCATION: (14)..(14)
<223> OTHER INFORMATION: Xaa can be phe or leu
<220> FEATURE:
<221> NAME/KEY: VARIANT
<222> LOCATION: (15)..(15)
<223> OTHER INFORMATION: Xaa is tyr
<220> FEATURE:
<221> NAME/KEY: VARIANT
<222> LOCATION: (16)..(16)
<223> OTHER INFORMATION: Xaa can be thr or ser
<220> FEATURE:
<221> NAME/KEY: VARIANT
<222> LOCATION: (17)..(17)
<223> OTHER INFORMATION: Xaa can be arg, lys or his
<220> FEATURE:
<221> NAME/KEY: VARIANT
<222> LOCATION: (18)..(18)
<223> OTHER INFORMATION: Xaa can be thr or ser
<220> FEATURE:
<221> NAME/KEY: VARIANT
<222> LOCATION: (19)..(19)
<223> OTHER INFORMATION: Xaa can be gln or asn
<220> FEATURE:
<221> NAME/KEY: VARIANT
<222> LOCATION: (20)..(20)
<223> OTHER INFORMATION: Xaa can be ser or thr
<220> FEATURE:
<221> NAME/KEY: VARIANT
<222> LOCATION: (21)..(21)
<223> OTHER INFORMATION: Xaa can be his, arg or lys
<220> FEATURE:
<221> NAME/KEY: VARIANT
<222> LOCATION: (22)..(22)
<223> OTHER INFORMATION: Xaa can be arg, lys or his
<220> FEATURE:
<221> NAME/KEY: VARIANT
<222> LOCATION: (23)..(23)
<223> OTHER INFORMATION: Xaa can be ser or thr
<220> FEATURE:
<221> NAME/KEY: VARIANT
<222> LOCATION: (24)..(24)
<223> OTHER INFORMATION: Xaa can be thr or ser
<220> FEATURE:
<221> NAME/KEY: VARIANT
<222> LOCATION: (25)..(25)
<223> OTHER INFORMATION: can be cys or met

<400> SEQUENCE: 1

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
```

20                  25

<210> SEQ ID NO 2
<211> LENGTH: 25
<212> TYPE: PRT
<213> ORGANISM: Artificial Sequence
<220> FEATURE:
<223> OTHER INFORMATION: Synthetic peptide

<400> SEQUENCE: 2

Leu Pro Leu Ser Arg His Tyr Gly Gly Gly Ser Val Pro Phe Tyr Ser
1               5                   10                  15

His Ser Asn Thr His His Thr Ser Met
            20                  25

<210> SEQ ID NO 3
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa can be lys, arg or his
<220> FEATURE:
<221> NAME/KEY: VARIANT
<222> LOCATION: (2)..(2)
<223> OTHER INFORMATION: Xaa can be glu or asp
<220> FEATURE:
<221> NAME/KEY: VARIANT
<222> LOCATION: (3)..(3)
<223> OTHER INFORMATION: Xaa can be lys, his or arg
<220> FEATURE:
<221> NAME/KEY: VARIANT
<222> LOCATION: (4)..(4)
<223> OTHER INFORMATION: Xaa can be ile or leu
<220> FEATURE:
<221> NAME/KEY: VARIANT
<222> LOCATION: (5)..(5)
<223> OTHER INFORMATION: Xaa can be arg, his or lys
<220> FEATURE:
<221> NAME/KEY: VARIANT
<222> LOCATION: (6)..(6)
<223> OTHER INFORMATION: Xaa can be thr or ser
<220> FEATURE:
<221> NAME/KEY: VARIANT
<222> LOCATION: (7)..(7)
<223> OTHER INFORMATION: Xaa can be lys, his or arg
<220> FEATURE:
<221> NAME/KEY: VARIANT
<222> LOCATION: (19)..(19)
<223> OTHER INFORMATION: Xaa can be leu or ile
<220> FEATURE:
<221> NAME/KEY: VARIANT
<222> LOCATION: (20)..(20)
<223> OTHER INFORMATION: Xaa can be lys, arg or his
<220> FEATURE:
<221> NAME/KEY: VARIANT
<222> LOCATION: (21)..(21)
<223> OTHER INFORMATION: Xaa is ala
<220> FEATURE:
<221> NAME/KEY: VARIANT
<222> LOCATION: (22)..(22)
<223> OTHER INFORMATION: Xaa can be lys, arg or his
<220> FEATURE:
<221> NAME/KEY: VARIANT
<222> LOCATION: (23)..(23)
<223> OTHER INFORMATION: can be ile or leu
<220> FEATURE:
<221> NAME/KEY: VARIANT
<222> LOCATION: (24)..(24)
<223> OTHER INFORMATION: Xaa is pro
<220> FEATURE:
<221> NAME/KEY: VARIANT

```
<222> LOCATION: (25)..(25)
<223> OTHER INFORMATION: Xaa can be asn or gln

<400> SEQUENCE: 3

Xaa Xaa Xaa Xaa Xaa Xaa Xaa Gly Gly Gly Ser Val Pro Phe Tyr Ser
1               5                   10                  15

His Ser Xaa Xaa Xaa Xaa Xaa Xaa Xaa
            20                  25

<210> SEQ ID NO 4
<211> LENGTH: 25
<212> TYPE: PRT
<213> ORGANISM: Artificial Sequence
<220> FEATURE:
<223> OTHER INFORMATION: Synthetic peptide

<400> SEQUENCE: 4

His Asp Arg Leu Lys Ser His Gly Gly Gly Ser Val Pro Phe Tyr Ser
1               5                   10                  15

His Ser Ile His Ala His Leu Pro Gln
            20                  25

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Leu Pro Leu Ser Arg His Tyr
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Asn Thr His His Thr Ser Met
1               5

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide

<400> SEQUENCE: 7

Gly Gly Gly Ser Val Pro Phe Tyr Ser His Ser
1               5                   10
```